US011204351B2

(12) United States Patent
Mehra et al.

(10) Patent No.: US 11,204,351 B2
(45) **Date of Patent: *Dec. 21, 2021**

(54) **COMPOSITIONS AND METHODS FOR IDENTIFYING *EHRLICHIA* SPECIES**

(71) Applicant: ZOETIS SERVICES LLC, Parsippany, NJ (US)

(72) Inventors: Rajesh K. Mehra, Hayward, CA (US); Jeremy D. Walker, Castro Valley, CA (US); Kenneth P. Aron, San Francisco, CA (US); Dennis M. Bleile, San Ramon, CA (US); Cristina R. Cuesico, Fremont, CA (US); Timothy P. Forsyth, Hayward, CA (US)

(73) Assignee: ZOETIS SERVICES LLC, Parsippany, NJ (US)

( * ) Notice: Subject to any disclaimer, the term of this patent is extended or adjusted under 35 U.S.C. 154(b) by 1063 days.

This patent is subject to a terminal disclaimer.

(21) Appl. No.: 15/812,052

(22) Filed: Nov. 14, 2017

(65) Prior Publication Data

US 2018/0067115 A1 Mar. 8, 2018

Related U.S. Application Data

(63) Continuation of application No. 15/226,108, filed on Aug. 2, 2016, now Pat. No. 9,851,352, which is a continuation of application No. 14/252,696, filed on Apr. 14, 2014, now Pat. No. 9,442,112.

(60) Provisional application No. 61/975,581, filed on Apr. 4, 2014.

(51) Int. Cl.
*G01N 33/569* (2006.01)

(52) U.S. Cl.
CPC ... *G01N 33/56911* (2013.01); *G01N 2333/29* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 4,366,246 | A | 12/1982 | Riggs |
| 4,617,262 | A | 10/1986 | Maxim |
| 6,204,252 | B1 | 3/2001 | Murphy et al. |
| 6,207,169 | B1 | 3/2001 | Reed et al. |
| 6,231,869 | B1 | 5/2001 | Reed et al. |
| 6,284,238 | B1 | 9/2001 | Coughlin et al. |
| 6,306,402 | B1 | 10/2001 | Reed et al. |
| 6,355,777 | B1 | 3/2002 | Walker et al. |
| 6,451,315 | B1 | 9/2002 | Reed et al. |
| 6,544,517 | B1 | 4/2003 | Rikihisa et al. |
| 6,593,147 | B1 | 7/2003 | Barbet et al. |
| 6,893,640 | B2 | 5/2005 | Rikihisa et al. |
| 6,923,963 | B2 | 8/2005 | Rikihisa et al. |
| 6,964,855 | B2 | 11/2005 | O'Connor et al. |
| 7,063,846 | B2 | 6/2006 | Rikihisa et al. |
| 7,087,372 | B2 | 8/2006 | Lawton et al. |
| 7,183,060 | B2 | 2/2007 | O'Connor, Jr. |
| 7,204,992 | B2 | 4/2007 | McBride et al. |
| 7,407,770 | B2 | 8/2008 | O'Connor, Jr. |
| 7,445,788 | B2 | 11/2008 | Lawton et al. |
| 7,449,191 | B2 | 11/2008 | Lawton et al. |
| 7,482,128 | B2 | 1/2009 | Jensen et al. |
| 7,709,622 | B2 | 5/2010 | Rikihisa et al. |
| 7,744,872 | B2 | 6/2010 | O'Connor, Jr. |
| 7,888,491 | B2 | 2/2011 | Rikihisa et al. |
| 8,158,751 | B2 | 4/2012 | O'Connor, Jr. |
| 8,828,675 | B2 | 9/2014 | Mehra et al. |
| 9,157,913 | B2 | 10/2015 | Mehra et al. |
| 9,442,112 | B2 | 9/2016 | Mehra et al. |
| 9,470,682 | B2 | 10/2016 | Mehra et al. |
| 9,651,546 | B2 | 5/2017 | Mehra et al. |
| 9,696,300 | B2 | 7/2017 | Mehra et al. |
| 9,851,352 | B2 | 12/2017 | Mehra et al. |
| 10,444,231 | B2 | 10/2019 | Mehra et al. |
| 2002/0120115 | A1 | 8/2002 | Rikihisa et al. |
| 2002/0132789 | A1 | 9/2002 | Barbet et al. |
| 2002/0160432 | A1 | 10/2002 | Lawton et al. |
| 2002/0177178 | A1 | 11/2002 | Lawton et al. |
| 2003/0022262 | A1 | 1/2003 | McDonald et al. |
| 2003/0103991 | A1 | 6/2003 | Rikihisa |
| 2003/0119082 | A1 | 6/2003 | Lawton et al. |
| 2003/0129161 | A1 | 7/2003 | Chu |
| 2005/0124015 | A1 | 6/2005 | O'Connor et al. |
| 2005/0142557 | A1 | 6/2005 | Alleman et al. |

(Continued)

FOREIGN PATENT DOCUMENTS

| | | |
|---|---|---|
| CN | 1321190 A | 11/2001 |
| CN | 1367832 A | 9/2002 |

(Continued)

OTHER PUBLICATIONS

Cardenas, A. M. et al., "Enzyme-Linked Immunosorbent Assay with Conserved Immunoreactive Glycoproteins gp36 and gp19 Has Enhanced Sensitivity and Provides Species-Specific Immunodiagnosis of Ehrlichia canis Infection," Clinical and Vaccine Immunology, 14(2):123-128 (2007).
Crocquet-Valdes, P. A. et al., "Immunization with Ehrlichia P28 Outer Membrane Proteins Confers Protection in a Mouse Model of Ehrlichiosis," Clinical and Vaccine Immunology, 18(12):2018-2025 (2011).
De Farias Rotondano, T. E. et al., "An assessment of whole blood and fractions by nested PCR as a DNA source for diagnosing canine ehrlichiosis and anaplasmosis," The Scientific World Journal, vol. 2012; Article ID 605743 (2012).

(Continued)

*Primary Examiner* — Christopher M Gross
(74) *Attorney, Agent, or Firm* — Cooley LLP

(57) ABSTRACT

The invention provides methods, kits, compositions, and devices useful for detection of antibodies that bind to *Ehrlichia* antigens and/or for differentiation of certain *Ehrlichia* species from others. In particular, the invention provides methods and kits useful for identifying species of *Ehrlichia* using populations of isolated peptides.

30 Claims, 2 Drawing Sheets

Specification includes a Sequence Listing.

(56) References Cited

U.S. PATENT DOCUMENTS

| | | | |
|---|---|---|---|
| 2006/0189537 | A1 | 8/2006 | O'Connor |
| 2006/0211062 | A1 | 9/2006 | O'Connor |
| 2006/0234322 | A1 | 10/2006 | Krah et al. |
| 2007/0020733 | A1 | 1/2007 | Lawton et al. |
| 2007/0026474 | A1 | 2/2007 | Lawton et al. |
| 2007/0161782 | A1 | 7/2007 | O'Connor |
| 2008/0248497 | A1 | 10/2008 | Beall et al. |
| 2009/0004217 | A1 | 1/2009 | Krah et al. |
| 2009/0010956 | A1 | 1/2009 | Rikihisa |
| 2009/0042222 | A1 | 2/2009 | O'Connor et al. |
| 2009/0081695 | A1 | 3/2009 | O'Connor et al. |
| 2009/0081708 | A1 | 3/2009 | O'Connor et al. |
| 2009/0098583 | A1 | 4/2009 | McDonald et al. |
| 2009/0110691 | A1 | 4/2009 | Krah et al. |
| 2009/0155825 | A1 | 6/2009 | Beall et al. |
| 2009/0176208 | A1 | 7/2009 | Brodie |
| 2010/0081125 | A1 | 4/2010 | Xia et al. |
| 2010/0267166 | A1 | 10/2010 | Nazareth et al. |
| 2011/0124125 | A1 | 5/2011 | Mehra et al. |
| 2014/0121125 | A1 | 5/2014 | Mehra et al. |
| 2014/0212898 | A1 | 7/2014 | Mehra et al. |
| 2015/0024417 | A1 | 1/2015 | Mehra et al. |
| 2015/0285797 | A1 | 10/2015 | Mehra et al. |
| 2016/0054313 | A1 | 2/2016 | Mehra et al. |
| 2017/0082622 | A1 | 3/2017 | Mehra et al. |

FOREIGN PATENT DOCUMENTS

| | | | |
|---|---|---|---|
| CN | 1473166 | A | 2/2004 |
| CN | 1735684 | | 2/2006 |
| CN | 101970463 | A | 2/2011 |
| CN | 103060468 | A | 4/2013 |
| EP | 1026949 | B1 | 9/2010 |
| EP | 2056112 | B1 | 3/2012 |
| JP | 2002-515763 | A | 5/2002 |
| JP | 2002-527042 | A | 8/2002 |
| JP | 2003-517282 | A | 5/2003 |
| JP | 2005-502586 | A | 1/2005 |
| JP | 2006-505270 | A | 2/2006 |
| WO | WO 1999/013720 | A1 | 3/1999 |
| WO | WO 2000/006744 | A1 | 2/2000 |
| WO | WO 2000/012688 | A1 | 3/2000 |
| WO | WO 2000/032745 | A2 | 6/2000 |
| WO | WO 2001/007625 | A2 | 2/2001 |
| WO | WO 2002/022782 | A2 | 3/2002 |
| WO | WO 2002/057794 | A2 | 7/2002 |
| WO | WO 2005/087803 | A1 | 9/2005 |
| WO | WO 2006/138509 | A2 | 12/2006 |
| WO | WO 2008/137881 | A2 | 11/2008 |
| WO | WO 2009/039414 | A2 | 3/2009 |
| WO | WO 2011/063235 | A2 | 5/2011 |
| WO | WO 2014/059274 | A1 | 4/2014 |
| WO | WO 2015/153949 | A2 | 10/2015 |

OTHER PUBLICATIONS

Doyle, C. K. et al., "Differentially Expressed and Secreted Major Immunoreactive Protein Orthologs of Ehrlichia canis and E. chaffeensis Elicit Early Antibody Responses to Epitopes on Glycosylated Tandem Repeats," Infect. Immun., 74(1):711-720(2006).

Eliasson, M. et al., "Chimeric IgG-binding receptors engineered from staphylococcal protein A and streptococcal protein G," J. Biol. Chem., 263(9):4323-4327 (1988).

EP 15772535.9, Extended European Search Report dated Sep. 7, 2017, 10 pages.

First Office Action and Search Report for Chinese Patent Application No. 201080061669.1, dated Dec. 4, 2013, 9 pages.

Gusa, A. A. et al., "28 kDa major outer membrane protein P28, partial [Ehrlichia ewingii]," Genbank Accession No. AAG44899.1 (Nov. 2001), 1 page.

Gusa, A. A. et al., "Identification of a p28 gene in Ehrlichia ewingii: evaluation of gene for use as a target for a species-specific PCR diagnostic assay," Journal of Clinical Microbiology, 39(11):3871-3876 (2001).

International Search Report and Written Opinion for International Application. No. PCT/US2010/057430, dated Aug. 10, 2011, 11 pages.

International Preliminary Report on Patentability for International Application. No. PCT/US2010/057430, dated May 22, 2012, 6 pages.

International Search Report and Written Opinion for International Application No. PCT/US2013/064536, dated Feb. 6, 2014, 9 pages.

International Preliminary Report on Patentability for International Application No. PCT/US2013/064536, dated Apr. 14, 2015, 7 pages.

International Search Report and Written Opinion for International Application No. PCT/US2015/024208, dated Jul. 20, 2015, 8 pages.

International Preliminary Report on Patentability for International Application No. PCT/US2015/024208, dated Oct. 4, 2016, 5 pages.

Knowles, T. T. et al., "Characterization of the major antigenic protein 2 of Ehrlichia canis and Ehrlichia chaffeensis and its application for serodiagnosis of ehrlichiosis," Clinical and Vaccine Immunology, 10(4):520-524 (2003).

Liddell, A. M. et al., "Predominance of Ehrlichia ewingii in Missouri dogs," J. Clin. Microbiol., 41(10):4617-4622 (2003).

Luo, T. et al., "Molecular Characterization of Antibody Epitopes of Ehrlichia chaffeensis Ankyrin Protein 200 and Tandem Repeat Protein 47 and Evaluation of Synthetic Immunodeterminants for Serodiagnosis of Human Monocytotropic Ehrlichiosis," Clinical and Vaccine Immunology, 17(1): 87-97 (2010).

McBride, J. W. et al., "Identification of a Glycosylated Ehrlichia canis 19-kilodalton major immunoreactive protein with a species-specific serine-rich glycopeptide epitope," Infection and Immunity, 75(1):74-82 (2007).

Nazari, M. et al., "Molecular Detection of Ehrlichia canis in Dogs in Malaysia," PLoS Negl. Trop. Dis., 7(1):e1982 (Jan. 2013).

Nilsson, J., et al., "Affinity fusion strategies for detection, purification, and immobilization of recombinant proteins." Protein Expr Purif. (1997); 11(1): 1-16.

Office Action for U.S. Appl. No. 12/950,707, dated Oct. 16, 2013, 7 pages.

Office Action for U.S. Appl. No. 14/252,690, dated Aug. 22, 2014, 20 pages.

Paddock, C. D. et al., "Ehrlichia chaffeensis: a prototypical emerging pathogen," Clin. Microbiol. Rev., 16(1):37-64 (2003).

Second Office Action for Chinese Patent Application No. 201080061669.1, dated Sep. 30, 2014, 4 pages.

Sirigireddy, K. R. et al., "Multiplex Detection of Ehrlichia and Anaplasma Species Pathogens in Peripheral Blood by Real-Time Reverse Transcriptase-Polymerase Chain Reaction," Journal of Molecular Diagnostics, 7(2):308-316 (May 2005).

Search Report in Chinese Application No. 201510582480.1, with English translation, dated Aug. 10, 2016, 4 pages.

Search Report in Chinese Application No. 201580023440.1, with English translation, dated Jun. 26, 2017, 4 pages.

Supplementary European Search Report for European Application No. 13844762.8, dated Apr. 25, 2016, 9 pages.

Supplementary European Search Report for European Application No. 10832262.9, dated Jan. 21, 2014, 7 pages.

Thomas, R. J. et al., "Current management of human granulocytic anaplasmosis, human monocytic ehrlichiosis and Ehrlichia ewingii Ehrlichiosis," Expert Rev. Anti. Infect. Ther., 7(6):709-722 (Aug. 2009).

Zhang, C. et al., "Identification of 19 polymorphic major outer membrane protein genes and their immunogenic peptides in Ehrlichia ewingii for use in a serodiagnostic assay," Clinical and Vaccine Immunology, 15(3): 402-411 (2008).

*Ehrlichia* Species Identification

SEQUENCE LISTING

```
<160> NUMBER OF SEQ ID NOS: 120

<210> SEQ ID NO 1
<211> LENGTH: 71
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: MISC_FEATURE
<222> LOCATION: (2)..(2)
<223> OTHER INFORMATION: Xaa may be Ala or Val
<220> FEATURE:
<221> NAME/KEY: MISC_FEATURE
<222> LOCATION: (5)..(5)
<223> OTHER INFORMATION: Xaa may be Glu or Asp
<220> FEATURE:
<221> NAME/KEY: MISC_FEATURE
<222> LOCATION: (8)..(8)
<223> OTHER INFORMATION: Xaa may be Thr or Pro
<220> FEATURE:
```

```
<221> NAME/KEY: MISC_FEATURE
<222> LOCATION: (10)..(10)
<223> OTHER INFORMATION: Xaa may be Thr or Val
<220> FEATURE:
<221> NAME/KEY: MISC_FEATURE
<222> LOCATION: (11)..(11)
<223> OTHER INFORMATION: Xaa may be Gly or Ala
<220> FEATURE:
<221> NAME/KEY: MISC_FEATURE
<222> LOCATION: (12)..(12)
<223> OTHER INFORMATION: Xaa may be Leu or Val
<220> FEATURE:
<221> NAME/KEY: MISC_FEATURE
<222> LOCATION: (13)..(13)
<223> OTHER INFORMATION: Xaa may be Tyr or Phe
<220> FEATURE:
<221> NAME/KEY: MISC_FEATURE
<222> LOCATION: (18)..(18)
<223> OTHER INFORMATION: Xaa may be Asp or Asn
<220> FEATURE:
<221> NAME/KEY: MISC_FEATURE
<222> LOCATION: (20)..(20)
<223> OTHER INFORMATION: Xaa may be Asp or Asn
<220> FEATURE:
<221> NAME/KEY: MISC_FEATURE
<222> LOCATION: (22)..(22)
<223> OTHER INFORMATION: Xaa may be Ser or Val
<220> FEATURE:
<221> NAME/KEY: MISC_FEATURE
<222> LOCATION: (23)..(23)
<223> OTHER INFORMATION: Xaa may be Ala, Ser or Thr
<220> FEATURE:
<221> NAME/KEY: MISC_FEATURE
<222> LOCATION: (24)..(24)
<223> OTHER INFORMATION: Xaa may be Ala or Ile
<220> FEATURE:
<221> NAME/KEY: MISC_FEATURE
<222> LOCATION: (25)..(25)
<223> OTHER INFORMATION: Xaa may be Thr or Pro
<220> FEATURE:
<221> NAME/KEY: MISC_FEATURE
<222> LOCATION: (26)..(26)
<223> OTHER INFORMATION: Xaa may be Ser, Asn or Lys
<220> FEATURE:
<221> NAME/KEY: MISC_FEATURE
<222> LOCATION: (39)..(39)
<223> OTHER INFORMATION: Xaa may be any amino acid
<220> FEATURE:
<221> NAME/KEY: MISC_FEATURE
<222> LOCATION: (44)..(44)
<223> OTHER INFORMATION: Xaa may be any amino acid
<220> FEATURE:
<221> NAME/KEY: MISC_FEATURE
<222> LOCATION: (49)..(49)
<223> OTHER INFORMATION: Xaa may be any amino acid
<220> FEATURE:
<221> NAME/KEY: MISC_FEATURE
<222> LOCATION: (56)..(56)
<223> OTHER INFORMATION: Xaa may be any amino acid
<220> FEATURE:
<221> NAME/KEY: MISC_FEATURE
<222> LOCATION: (58)..(58)
<223> OTHER INFORMATION: Xaa may be any amino acid

<400> SEQUENCE: 1

Ser Xaa Lys Glu Xaa Lys Gln Xaa Thr Xaa Xaa Xaa Xaa Gly Leu Lys
1               5                   10                  15

Gln Xaa Trp Xaa Gly Xaa Xaa Xaa Xaa Xaa Gly Gly Gly Gly Gly Asn
            20                  25                  30

Phe Ser Ala Lys Glu Glu Xaa Ala Glu Thr Arg Xaa Thr Phe Gly Leu
        35                  40                  45

Xaa Lys Gln Tyr Asp Gly Ala Xaa Ile Xaa Glu Asn Gln Val Gln Asn
    50                  55                  60

Lys Phe Thr Ile Ser Asn Cys
```

65 70

<210> SEQ ID NO 2
<211> LENGTH: 39
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: MISC_FEATURE
<222> LOCATION: (7)..(7)
<223> OTHER INFORMATION: Xaa may be any amino acid
<220> FEATURE:
<221> NAME/KEY: MISC_FEATURE
<222> LOCATION: (12)..(12)
<223> OTHER INFORMATION: Xaa may be any amino acid
<220> FEATURE:
<221> NAME/KEY: MISC_FEATURE
<222> LOCATION: (17)..(17)
<223> OTHER INFORMATION: Xaa may be any amino acid
<220> FEATURE:
<221> NAME/KEY: MISC_FEATURE
<222> LOCATION: (24)..(24)
<223> OTHER INFORMATION: Xaa may be any amino acid
<220> FEATURE:
<221> NAME/KEY: MISC_FEATURE
<222> LOCATION: (26)..(26)
<223> OTHER INFORMATION: Xaa may be any amino acid

<400> SEQUENCE: 2

Phe Ser Ala Lys Glu Glu Xaa Ala Glu Thr Arg Xaa Thr Phe Gly Leu
1 5 10 15

Xaa Lys Gln Tyr Asp Gly Ala Xaa Ile Xaa Glu Asn Gln Val Gln Asn
20 25 30

Lys Phe Thr Ile Ser Asn Cys
35

<210> SEQ ID NO 3
<211> LENGTH: 71
<212> TYPE: PRT
<213> ORGANISM: Artificial Sequence
<220> FEATURE:
<223> OTHER INFORMATION: Ehrlichia antigenic peptide
<220> FEATURE:
<221> NAME/KEY: MISC_FEATURE
<222> LOCATION: (2)..(2)
<223> OTHER INFORMATION: Xaa may be Ala or Val
<220> FEATURE:
<221> NAME/KEY: MISC_FEATURE
<222> LOCATION: (5)..(5)
<223> OTHER INFORMATION: Xaa may be Glu or Asp
<220> FEATURE:
<221> NAME/KEY: MISC_FEATURE
<222> LOCATION: (8)..(8)
<223> OTHER INFORMATION: Xaa may be Thr or Pro
<220> FEATURE:
<221> NAME/KEY: MISC_FEATURE
<222> LOCATION: (10)..(10)
<223> OTHER INFORMATION: Xaa may be Thr or Val
<220> FEATURE:
<221> NAME/KEY: MISC_FEATURE
<222> LOCATION: (11)..(11)
<223> OTHER INFORMATION: Xaa may be Gly or Ala
<220> FEATURE:
<221> NAME/KEY: MISC_FEATURE
<222> LOCATION: (12)..(12)
<223> OTHER INFORMATION: Xaa may be Leu or Val
<220> FEATURE:
<221> NAME/KEY: MISC_FEATURE
<222> LOCATION: (13)..(13)
<223> OTHER INFORMATION: Xaa may be Tyr of Phe
<220> FEATURE:
<221> NAME/KEY: MISC_FEATURE
<222> LOCATION: (18)..(18)

<223> OTHER INFORMATION: Xaa may be Asp or Asn
<220> FEATURE:
<221> NAME/KEY: MISC_FEATURE
<222> LOCATION: (20)..(20)
<223> OTHER INFORMATION: Xaa may be Asp or Asn
<220> FEATURE:
<221> NAME/KEY: MISC_FEATURE
<222> LOCATION: (22)..(22)
<223> OTHER INFORMATION: Xaa may be Ser or Val
<220> FEATURE:
<221> NAME/KEY: MISC_FEATURE
<222> LOCATION: (23)..(23)
<223> OTHER INFORMATION: Xaa may be Ala, Ser or Thr
<220> FEATURE:
<221> NAME/KEY: MISC_FEATURE
<222> LOCATION: (24)..(24)
<223> OTHER INFORMATION: Xaa may be Ala or Ile
<220> FEATURE:
<221> NAME/KEY: MISC_FEATURE
<222> LOCATION: (25)..(25)
<223> OTHER INFORMATION: Xaa may be Thr or Pro
<220> FEATURE:
<221> NAME/KEY: MISC_FEATURE
<222> LOCATION: (26)..(26)
<223> OTHER INFORMATION: Xaa may be Ser, Asn or Lys
<220> FEATURE:
<221> NAME/KEY: MISC_FEATURE
<222> LOCATION: (39)..(39)
<223> OTHER INFORMATION: Xaa may be any amino acid
<220> FEATURE:
<221> NAME/KEY: MISC_FEATURE
<222> LOCATION: (41)..(41)
<223> OTHER INFORMATION: Xaa may be Asp or Asn
<220> FEATURE:
<221> NAME/KEY: MISC_FEATURE
<222> LOCATION: (44)..(44)
<223> OTHER INFORMATION: Xaa may be any amino acid
<220> FEATURE:
<221> NAME/KEY: MISC_FEATURE
<222> LOCATION: (48)..(48)
<223> OTHER INFORMATION: Xaa may be Val or Ala
<220> FEATURE:
<221> NAME/KEY: MISC_FEATURE
<222> LOCATION: (49)..(49)
<223> OTHER INFORMATION: Xaa may be any amino acid
<220> FEATURE:
<221> NAME/KEY: MISC_FEATURE
<222> LOCATION: (56)..(56)
<223> OTHER INFORMATION: Xaa may be any amino acid
<220> FEATURE:
<221> NAME/KEY: MISC_FEATURE
<222> LOCATION: (58)..(58)
<223> OTHER INFORMATION: Xaa may be any amino acid

<400> SEQUENCE: 3

```
Ser Xaa Lys Glu Xaa Lys Gln Xaa Thr Xaa Xaa Xaa Xaa Gly Leu Lys
1               5                   10                  15

Gln Xaa Trp Xaa Gly Xaa Xaa Xaa Xaa Xaa Gly Gly Gly Gly Gly Asn
            20                  25                  30

Phe Ser Ala Lys Glu Glu Xaa Ala Xaa Thr Arg Xaa Thr Phe Gly Xaa
        35                  40                  45

Xaa Lys Gln Tyr Asp Gly Ala Xaa Ile Xaa Glu Asn Gln Val Gln Asn
    50                  55                  60

Lys Phe Thr Ile Ser Asn Cys
65                  70
```

<210> SEQ ID NO 4
<211> LENGTH: 71
<212> TYPE: PRT
<213> ORGANISM: Artificial Sequence
<220> FEATURE:
<223> OTHER INFORMATION: Ehrlichia antigenic peptide -continued

<400> SEQUENCE: 4

Ser Ala Lys Glu Glu Lys Gln Thr Thr Thr Gly Leu Tyr Gly Leu Lys
1 5 10 15

Gln Asp Trp Asp Gly Ser Ala Ala Thr Ser Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 5
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 5

Ser Ala Lys Glu Glu Lys Gln Thr Thr Thr Gly Leu Tyr Gly Leu Lys
1 5 10 15

Gln Asp Trp Asp Gly Ser Ala Ala Thr Ser Gly Gly Gly Gly Gly Asn
20 25 30

Phe Ser Ala Lys Glu Glu Lys Ala Glu Thr Arg Arg Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 6
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 6

Ser Ala Lys Glu Glu Lys Gln Thr Thr Thr Gly Leu Tyr Gly Leu Lys
1 5 10 15

Gln Asp Trp Asp Gly Ser Ala Ala Thr Ser Gly Gly Gly Gly Gly Asn
20 25 30

Phe Ser Ala Lys Glu Glu Lys Ala Glu Thr Arg Arg Thr Phe Gly Leu
35 40 45

Asp Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 7
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 7

Ser Ala Lys Glu Glu Lys Gln Thr Thr Thr Gly Leu Tyr Gly Leu Lys
1 5 10 15

```
Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Arg Thr Phe Gly Leu
        35                  40                  45

Glu Lys Gln Tyr Asp Gly Ala Gln Ile Glu Glu Asn Gln Val Gln Asn
    50                  55                  60

Lys Phe Thr Ile Ser Asn Cys
65                  70


<210> SEQ ID NO 8
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 8

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Asp Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 9
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 9

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Asp Lys Gln Tyr Asp Gly Ala Gln Ile Glu Glu Asn Gln Val Gln Asn
    50                  55                  60

Lys Phe Thr Ile Ser Asn Cys
65                  70


<210> SEQ ID NO 10
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 10

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30
```

```
Phe Ser Ala Lys Glu Glu Lys Ala Glu Thr Arg Lys Thr Phe Gly Leu
        35                  40                  45

Glu Lys Gln Tyr Asp Gly Ala Gln Ile Glu Glu Asn Gln Val Gln Asn
    50                  55                  60

Lys Phe Thr Ile Ser Asn Cys
65                  70


<210> SEQ ID NO 11
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 11

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Thr Glu Asn Gln Val Gln Asn
    50                  55                  60

Lys Phe Thr Ile Ser Asn Cys
65                  70


<210> SEQ ID NO 12
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 12

Ser Val Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Thr Glu Asn Gln Val Gln Asn
    50                  55                  60

Lys Phe Thr Ile Ser Asn Cys
65                  70


<210> SEQ ID NO 13
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 13

Ser Ala Lys Glu Asp Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Thr Glu Asn Gln Val Gln Asn
```

```
    50                  55                  60

Lys Phe Thr Ile Ser Asn Cys
65                  70


<210> SEQ ID NO 14
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 14

Ser Val Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 15
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 15

Ser Val Lys Glu Asp Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 16
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 16

Ser Ala Lys Glu Asp Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 17
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 17

```
Ser Ala Lys Glu Glu Lys Gln Pro Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 18
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 18

```
Ser Ala Lys Glu Glu Lys Gln Pro Thr Thr Ala Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 19
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 19

```
Ser Ala Lys Glu Glu Lys Gln Pro Thr Thr Gly Val Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 20
<211> LENGTH: 71

```
<212> TYPE: PRT
<213> ORGANISM: Artificial Sequence
<220> FEATURE:
<223> OTHER INFORMATION: Ehrlichia antigenic peptide

<400> SEQUENCE: 20

Ser Ala Lys Glu Glu Lys Gln Thr Thr Thr Ala Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 21
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 21

Ser Ala Lys Glu Glu Lys Gln Thr Thr Thr Ala Val Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 22
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 22

Ser Ala Lys Glu Glu Lys Gln Thr Thr Thr Gly Val Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 23
<211> LENGTH: 71
<212> TYPE: PRT
<213> ORGANISM: Artificial Sequence
<220> FEATURE:
<223> OTHER INFORMATION: Ehrlichia antigenic peptide
```

<400> SEQUENCE: 23

Ser Ala Lys Glu Glu Lys Gln Thr Thr Thr Gly Leu Phe Gly Leu Lys
1 5 10 15

Gln Asp Trp Asp Gly Ser Ala Ala Thr Ser Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 24
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 24

Ser Ala Lys Glu Glu Lys Gln Thr Thr Thr Gly Leu Phe Gly Leu Lys
1 5 10 15

Gln Asn Trp Asp Gly Ser Ala Ala Thr Ser Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 25
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 25

Ser Ala Lys Glu Glu Lys Gln Thr Thr Thr Gly Leu Phe Gly Leu Lys
1 5 10 15

Gln Asp Trp Asn Gly Ser Ala Ala Thr Ser Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 26
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 26

Ser Ala Lys Glu Glu Lys Gln Thr Thr Thr Gly Leu Tyr Gly Leu Lys

```
1               5                   10                  15

Gln Asn Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 27
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 27

Ser Ala Lys Glu Glu Lys Gln Thr Thr Thr Gly Leu Tyr Gly Leu Lys
1               5                   10                  15

Gln Asn Trp Asn Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 28
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 28

Ser Ala Lys Glu Glu Lys Gln Thr Thr Thr Gly Leu Tyr Gly Leu Lys
1               5                   10                  15

Gln Asp Trp Asn Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 29
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 29

Ser Ala Lys Glu Glu Lys Gln Thr Thr Thr Gly Leu Tyr Gly Leu Lys
1               5                   10                  15

Gln Asp Trp Asp Gly Val Ala Ala Thr Ser Gly Gly Gly Gly Gly Asn
            20                  25                  30
```

```
Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 30
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 30

Ser Ala Lys Glu Glu Lys Gln Thr Thr Thr Gly Leu Tyr Gly Leu Lys
1               5                   10                  15

Gln Asp Trp Asp Gly Val Ser Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 31
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 31

Ser Ala Lys Glu Glu Lys Gln Thr Thr Thr Gly Leu Tyr Gly Leu Lys
1               5                   10                  15

Gln Asp Trp Asp Gly Val Thr Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 32
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 32

Ser Ala Lys Glu Glu Lys Gln Thr Thr Thr Gly Leu Tyr Gly Leu Lys
1               5                   10                  15

Gln Asp Trp Asp Gly Ser Ser Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45
```

-continued

```
Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 33
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 33

```
Ser Ala Lys Glu Glu Lys Gln Thr Thr Thr Gly Leu Tyr Gly Leu Lys
1               5                   10                  15

Gln Asp Trp Asp Gly Ser Thr Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 34
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 34

```
Ser Ala Lys Glu Glu Lys Gln Thr Thr Thr Gly Leu Tyr Gly Leu Lys
1               5                   10                  15

Gln Asp Trp Asp Gly Ser Ser Ile Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 35
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 35

```
Ser Ala Lys Glu Glu Lys Gln Thr Thr Thr Gly Leu Tyr Gly Leu Lys
1               5                   10                  15

Gln Asp Trp Asp Gly Ser Thr Ile Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
```

65 70

<210> SEQ ID NO 36
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 36

Ser Ala Lys Glu Glu Lys Gln Thr Thr Thr Gly Leu Tyr Gly Leu Lys
1 5 10 15

Gln Asp Trp Asp Gly Ser Ala Ile Thr Ser Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 37
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 37

Ser Ala Lys Glu Glu Lys Gln Thr Thr Thr Gly Leu Tyr Gly Leu Lys
1 5 10 15

Gln Asp Trp Asp Gly Ser Ala Ala Pro Ser Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 38
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 38

Ser Ala Lys Glu Glu Lys Gln Thr Thr Thr Gly Leu Tyr Gly Leu Lys
1 5 10 15

Gln Asp Trp Asp Gly Ser Ala Ala Pro Asn Gly Gly Gly Gly Gly Asn
20 25 30

Phe Ser Ala Lys Glu Glu Lys Ala Glu Thr Arg Lys Thr Phe Gly Leu
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 39

<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 39

```
Ser Ala Lys Glu Glu Lys Gln Thr Thr Thr Gly Leu Tyr Gly Leu Lys
1               5                   10                  15

Gln Asp Trp Asp Gly Ser Ala Ala Pro Lys Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 40
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 40

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Asn Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 41
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 41

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Lys Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 42
<211> LENGTH: 71
<212> TYPE: PRT
<213> ORGANISM: Artificial Sequence
<220> FEATURE:

-continued

<223> OTHER INFORMATION: Ehrlichia antigenic peptide

<400> SEQUENCE: 42

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Asn Gly Gly Gly Gly Gly Asn
            20                  25                  30

Phe Ser Ala Lys Glu Glu Lys Ala Glu Thr Arg Arg Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 43
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 43

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Lys Gly Gly Gly Gly Gly Asn
            20                  25                  30

Phe Ser Ala Lys Glu Glu Lys Ala Glu Thr Arg Arg Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 44
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 44

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Arg Ala Glu Thr Arg Lys Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 45
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 45

-continued

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Gln Thr Phe Gly Leu
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 46
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 46

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Gln Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 47
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 47

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Asn Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 48
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 48

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
```

```
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Arg Ile Glu Glu Asn Gln Val Gln Asn
    50                  55                  60

Lys Phe Thr Ile Ser Asn Cys
65                  70


<210> SEQ ID NO 49
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 49

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Glu Ile Glu Glu Asn Gln Val Gln Asn
    50                  55                  60

Lys Phe Thr Ile Ser Asn Cys
65                  70


<210> SEQ ID NO 50
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 50

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45

Glu Lys Gln Tyr Asp Gly Ala Lys Ile Asp Glu Asn Gln Val Gln Asn
    50                  55                  60

Lys Phe Thr Ile Ser Asn Cys
65                  70


<210> SEQ ID NO 51
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 51

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Glu Thr Arg Lys Thr Phe Gly Leu
        35                  40                  45
```

```
Glu Lys Gln Tyr Asp Gly Ala Lys Ile Ser Glu Asn Gln Val Gln Asn
    50                  55                  60

Lys Phe Thr Ile Ser Asn Cys
65                  70


<210> SEQ ID NO 52
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 52

Phe Ser Ala Lys Glu Glu Lys Ala Glu Thr Arg Lys Thr Phe Gly Leu
1               5                   10                  15

Glu Lys Gln Tyr Asp Gly Ala Lys Ile Glu Glu Asn Gln Val Gln Asn
            20                  25                  30

Lys Phe Thr Ile Ser Asn Cys
        35


<210> SEQ ID NO 53
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 53

Phe Ser Ala Lys Glu Glu Lys Ala Glu Thr Arg Arg Thr Phe Gly Leu
1               5                   10                  15

Glu Lys Gln Tyr Asp Gly Ala Lys Ile Glu Glu Asn Gln Val Gln Asn
            20                  25                  30

Lys Phe Thr Ile Ser Asn Cys
        35


<210> SEQ ID NO 54
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 54

Phe Ser Ala Lys Glu Glu Lys Ala Glu Thr Arg Arg Thr Phe Gly Leu
1               5                   10                  15

Glu Lys Gln Tyr Asp Gly Ala Gln Ile Glu Glu Asn Gln Val Gln Asn
            20                  25                  30

Lys Phe Thr Ile Ser Asn Cys
        35


<210> SEQ ID NO 55
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 55

Phe Ser Ala Lys Glu Glu Lys Ala Glu Thr Arg Arg Thr Phe Gly Leu
1               5                   10                  15

Glu Lys Gln Tyr Asp Gly Ala Lys Ile Thr Glu Asn Gln Val Gln Asn
            20                  25                  30
```

```
Lys Phe Thr Ile Ser Asn Cys
        35


<210> SEQ ID NO 56
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 56

Phe Ser Ala Lys Glu Glu Lys Ala Glu Thr Arg Lys Thr Phe Gly Leu
1               5                   10                  15

Glu Lys Gln Tyr Asp Gly Ala Gln Ile Glu Glu Asn Gln Val Gln Asn
            20                  25                  30

Lys Phe Thr Ile Ser Asn Cys
        35


<210> SEQ ID NO 57
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 57

Phe Ser Ala Lys Glu Glu Lys Ala Glu Thr Arg Lys Thr Phe Gly Leu
1               5                   10                  15

Glu Lys Gln Tyr Asp Gly Ala Gln Ile Thr Glu Asn Gln Val Gln Asn
            20                  25                  30

Lys Phe Thr Ile Ser Asn Cys
        35


<210> SEQ ID NO 58
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 58

Phe Ser Ala Lys Glu Glu Lys Ala Glu Thr Arg Lys Thr Phe Gly Leu
1               5                   10                  15

Glu Lys Gln Tyr Asp Gly Ala Lys Ile Thr Glu Asn Gln Val Gln Asn
            20                  25                  30

Lys Phe Thr Ile Ser Asn Cys
        35


<210> SEQ ID NO 59
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 59

Phe Ser Ala Lys Glu Glu Arg Ala Glu Thr Arg Lys Thr Phe Gly Leu
1               5                   10                  15

Glu Lys Gln Tyr Asp Gly Ala Lys Ile Glu Glu Asn Gln Val Gln Asn
            20                  25                  30

Lys Phe Thr Ile Ser Asn Cys
        35
```

<210> SEQ ID NO 60
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 60

```
Phe Ser Ala Lys Glu Glu Lys Ala Glu Thr Arg Gln Thr Phe Gly Leu
1               5                   10                  15

Glu Lys Gln Tyr Asp Gly Ala Lys Ile Glu Glu Asn Gln Val Gln Asn
            20                  25                  30

Lys Phe Thr Ile Ser Asn Cys
        35
```

<210> SEQ ID NO 61
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 61

```
Phe Ser Ala Lys Glu Glu Lys Ala Glu Thr Arg Lys Thr Phe Gly Leu
1               5                   10                  15

Gln Lys Gln Tyr Asp Gly Ala Lys Ile Glu Glu Asn Gln Val Gln Asn
            20                  25                  30

Lys Phe Thr Ile Ser Asn Cys
        35
```

<210> SEQ ID NO 62
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 62

```
Phe Ser Ala Lys Glu Glu Lys Ala Glu Thr Arg Lys Thr Phe Gly Leu
1               5                   10                  15

Asn Lys Gln Tyr Asp Gly Ala Lys Ile Glu Glu Asn Gln Val Gln Asn
            20                  25                  30

Lys Phe Thr Ile Ser Asn Cys
        35
```

<210> SEQ ID NO 63
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 63

```
Phe Ser Ala Lys Glu Glu Lys Ala Glu Thr Arg Lys Thr Phe Gly Leu
1               5                   10                  15

Glu Lys Gln Tyr Asp Gly Ala Arg Ile Glu Glu Asn Gln Val Gln Asn
            20                  25                  30

Lys Phe Thr Ile Ser Asn Cys
        35
```

<210> SEQ ID NO 64

```
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 64

Phe Ser Ala Lys Glu Glu Lys Ala Glu Thr Arg Lys Thr Phe Gly Leu
1               5                   10                  15

Glu Lys Gln Tyr Asp Gly Ala Glu Ile Glu Glu Asn Gln Val Gln Asn
            20                  25                  30

Lys Phe Thr Ile Ser Asn Cys
        35


<210> SEQ ID NO 65
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 65

Phe Ser Ala Lys Glu Glu Lys Ala Glu Thr Arg Lys Thr Phe Gly Leu
1               5                   10                  15

Glu Lys Gln Tyr Asp Gly Ala Lys Ile Asp Glu Asn Gln Val Gln Asn
            20                  25                  30

Lys Phe Thr Ile Ser Asn Cys
        35


<210> SEQ ID NO 66
<211> LENGTH: 39
<212> TYPE: PRT
<213> ORGANISM: Artificial Sequence
<220> FEATURE:
<223> OTHER INFORMATION: Ehrlichia antigenic peptide

<400> SEQUENCE: 66

Phe Ser Ala Lys Glu Glu Lys Ala Glu Thr Arg Lys Thr Phe Gly Leu
1               5                   10                  15

Glu Lys Gln Tyr Asp Gly Ala Lys Ile Ser Glu Asn Gln Val Gln Asn
            20                  25                  30

Lys Phe Thr Ile Ser Asn Cys
        35


<210> SEQ ID NO 67
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 67

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 68
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 68

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Arg Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 69
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 69

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Arg Thr Phe Gly Val
        35                  40                  45

Asp Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 70
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 70

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Arg Thr Phe Gly Val
        35                  40                  45

Glu Lys Gln Tyr Asp Gly Ala Gln Ile Glu Glu Asn Gln Val Gln Asn
    50                  55                  60

Lys Phe Thr Ile Ser Asn Cys
65                  70
```

<210> SEQ ID NO 71
<211> LENGTH: 71

```
<212> TYPE: PRT
<213> ORGANISM: Artificial Sequence
<220> FEATURE:
<223> OTHER INFORMATION: Ehrlichia antigenic peptide

<400> SEQUENCE: 71

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Asp Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 72
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 72

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Asp Lys Gln Tyr Asp Gly Ala Gln Ile Glu Glu Asn Gln Val Gln Asn
    50                  55                  60

Lys Phe Thr Ile Ser Asn Cys
65                  70


<210> SEQ ID NO 73
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 73

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Gln Ile Glu Glu Asn Gln Val Gln Asn
    50                  55                  60

Lys Phe Thr Ile Ser Asn Cys
65                  70


<210> SEQ ID NO 74
<211> LENGTH: 71
<212> TYPE: PRT
<213> ORGANISM: Artificial Sequence
<220> FEATURE:
<223> OTHER INFORMATION: Ehrlichia antigenic peptide
```

<400> SEQUENCE: 74

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Thr Glu Asn Gln Val Gln Asn
    50                  55                  60

Lys Phe Thr Ile Ser Asn Cys
65                  70

<210> SEQ ID NO 75
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 75

Ser Val Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Thr Glu Asn Gln Val Gln Asn
    50                  55                  60

Lys Phe Thr Ile Ser Asn Cys
65                  70

<210> SEQ ID NO 76
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 76

Ser Ala Lys Glu Asp Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Thr Glu Asn Gln Val Gln Asn
    50                  55                  60

Lys Phe Thr Ile Ser Asn Cys
65                  70

<210> SEQ ID NO 77
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 77

Ser Val Lys Glu Glu Lys Gln Thr Thr Thr Gly Leu Tyr Gly Leu Lys

-continued

```
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 78
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 78

Ser Val Lys Glu Asp Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 79
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 79

Ser Ala Lys Glu Asp Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 80
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 80

Ser Ala Lys Glu Glu Lys Gln Pro Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30
```

```
Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 81
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 81

Ser Ala Lys Glu Glu Lys Gln Pro Thr Val Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 82
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 82

Ser Ala Lys Glu Glu Lys Gln Pro Thr Thr Ala Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 83
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 83

Ser Ala Lys Glu Glu Lys Gln Thr Thr Val Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45
```

-continued

```
Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 84
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 84

Ser Ala Lys Glu Glu Lys Gln Thr Thr Val Ala Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 85
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 85

Ser Ala Lys Glu Glu Lys Gln Thr Thr Thr Ala Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 86
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 86

Ser Ala Lys Glu Glu Lys Gln Thr Thr Thr Gly Val Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
```

65 70

<210> SEQ ID NO 87
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 87

Ser Ala Lys Glu Glu Lys Gln Thr Thr Thr Gly Val Phe Gly Leu Lys
1 5 10 15

Gln Asp Trp Asp Gly Ser Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 88
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 88

Ser Ala Lys Glu Glu Lys Gln Thr Thr Thr Gly Val Tyr Gly Leu Lys
1 5 10 15

Gln Asn Trp Asp Gly Ser Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 89
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 89

Ser Ala Lys Glu Glu Lys Gln Thr Thr Thr Gly Leu Phe Gly Leu Lys
1 5 10 15

Gln Asp Trp Asp Gly Ser Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 90

<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 90

Ser Ala Lys Glu Glu Lys Gln Thr Thr Thr Gly Leu Phe Gly Leu Lys
1 5 10 15

Gln Asn Trp Asp Gly Ser Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 91
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 91

Ser Ala Lys Glu Glu Lys Gln Thr Thr Thr Gly Leu Tyr Gly Leu Lys
1 5 10 15

Gln Asn Trp Asp Gly Ser Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 92
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 92

Ser Ala Lys Glu Glu Lys Gln Thr Thr Thr Gly Leu Tyr Gly Leu Lys
1 5 10 15

Gln Asp Trp Asn Gly Ser Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 93
<211> LENGTH: 71
<212> TYPE: PRT
<213> ORGANISM: Artificial Sequence
<220> FEATURE:

<223> OTHER INFORMATION: Ehrlichia antigenic peptide

<400> SEQUENCE: 93

Ser Ala Lys Glu Glu Lys Gln Thr Thr Thr Gly Leu Tyr Gly Leu Lys
1 5 10 15

Gln Asp Trp Asn Gly Ser Ser Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 94
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 94

Ser Ala Lys Glu Glu Lys Gln Thr Thr Thr Gly Leu Tyr Gly Leu Lys
1 5 10 15

Gln Asp Trp Asn Gly Ser Thr Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 95
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 95

Ser Ala Lys Glu Glu Lys Gln Thr Thr Thr Gly Leu Tyr Gly Leu Lys
1 5 10 15

Gln Asp Trp Asp Gly Val Ala Ala Thr Ser Gly Gly Gly Gly Gly Asn
20 25 30

Phe Ser Ala Lys Glu Glu Lys Ala Asp Thr Arg Lys Thr Phe Gly Val
35 40 45

Glu Lys Gln Tyr Asp Gly Ala Lys Ile Glu Glu Asn Gln Val Gln Asn
50 55 60

Lys Phe Thr Ile Ser Asn Cys
65 70

<210> SEQ ID NO 96
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 96

-continued

```
Ser Ala Lys Glu Glu Lys Gln Thr Thr Thr Gly Leu Tyr Gly Leu Lys
1               5                   10                  15

Gln Asp Trp Asp Gly Val Ser Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 97
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 97

Ser Ala Lys Glu Glu Lys Gln Thr Thr Thr Gly Leu Tyr Gly Leu Lys
1               5                   10                  15

Gln Asp Trp Asp Gly Val Thr Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 98
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 98

Ser Ala Lys Glu Glu Lys Gln Thr Thr Thr Gly Leu Tyr Gly Leu Lys
1               5                   10                  15

Gln Asp Trp Asp Gly Ser Ser Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 99
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 99

Ser Ala Lys Glu Glu Lys Gln Thr Thr Thr Gly Leu Tyr Gly Leu Lys
1               5                   10                  15

Gln Asp Trp Asp Gly Ser Thr Ala Thr Ser Gly Gly Gly Gly Gly Asn
```

```
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 100
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 100

Ser Ala Lys Glu Glu Lys Gln Thr Thr Thr Gly Leu Tyr Gly Leu Lys
1               5                   10                  15

Gln Asp Trp Asp Gly Ser Ala Ile Thr Asn Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 101
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 101

Ser Ala Lys Glu Glu Lys Gln Thr Thr Thr Gly Leu Tyr Gly Leu Lys
1               5                   10                  15

Gln Asp Trp Asp Gly Ser Ala Ile Thr Lys Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 102
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 102

Ser Ala Lys Glu Glu Lys Gln Thr Thr Thr Gly Leu Tyr Gly Leu Lys
1               5                   10                  15

Gln Asp Trp Asp Gly Ser Ala Ile Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45
```

```
Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 103
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 103

Ser Ala Lys Glu Glu Lys Gln Thr Thr Thr Gly Leu Tyr Gly Leu Lys
1               5                   10                  15

Gln Asp Trp Asp Gly Ser Ala Ala Pro Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 104
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 104

Ser Ala Lys Glu Glu Lys Gln Thr Thr Thr Gly Leu Tyr Gly Leu Lys
1               5                   10                  15

Gln Asp Trp Asp Gly Ser Ala Ala Pro Asn Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 105
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 105

Ser Ala Lys Glu Glu Lys Gln Thr Thr Thr Gly Leu Tyr Gly Leu Lys
1               5                   10                  15

Gln Asp Trp Asp Gly Ser Ala Ala Pro Lys Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60
```

```
Lys Phe Thr Ile Ser Asn Cys
65                  70


<210> SEQ ID NO 106
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 106

Ser Ala Lys Glu Glu Lys Gln Thr Thr Thr Gly Leu Tyr Gly Leu Lys
1               5                   10                  15

Gln Asp Trp Asp Gly Ser Ala Ala Thr Asn Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 107
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 107

Ser Ala Lys Glu Glu Lys Gln Thr Thr Thr Gly Leu Tyr Gly Leu Lys
1               5                   10                  15

Gln Asp Trp Asp Gly Ser Ala Ala Thr Lys Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 108
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 108

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asn Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 109
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 109

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asn Thr Arg Lys Thr Phe Gly Ala
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 110
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 110

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asn Thr Arg Lys Thr Phe Gly Val
        35                  40                  45

Asp Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 111
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 111

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Ala
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70
```

<210> SEQ ID NO 112
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 112

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Ala
        35                  40                  45

Asp Lys Gln Tyr Asp Gly Ala Lys Ile Glu Glu Asn Gln Val Gln Asn
    50                  55                  60

Lys Phe Thr Ile Ser Asn Cys
65                  70

<210> SEQ ID NO 113
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 113

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Arg Ala Asp Thr Arg Lys Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70

<210> SEQ ID NO 114
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 114

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Gln Thr Phe Gly Val
        35                  40                  45

Glu Lys Gln Tyr Asp Gly Ala Lys Ile Glu Glu Asn Gln Val Gln Asn
    50                  55                  60

Lys Phe Thr Ile Ser Asn Cys
65                  70

<210> SEQ ID NO 115
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 115

```
Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Gln Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 116
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 116

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Asn Lys Gln Tyr Asp Gly Ala Lys Ile Glu Glu Asn Gln Val Gln Asn
    50                  55                  60

Lys Phe Thr Ile Ser Asn Cys
65                  70


<210> SEQ ID NO 117
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 117

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Arg Ile Glu Glu Asn Gln Val Gln Asn
    50                  55                  60

Lys Phe Thr Ile Ser Asn Cys
65                  70


<210> SEQ ID NO 118
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 118

Ser Ala Lys Glu Glu Lys Gln Thr Thr Thr Gly Leu Tyr Gly Leu Lys
1               5                   10                  15
```

-continued

```
Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Glu Ile Glu Glu Asn Gln Val Gln Asn
    50                  55                  60

Lys Phe Thr Ile Ser Asn Cys
65                  70


<210> SEQ ID NO 119
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 119

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Asp Glu Asn Gln Val Gln Asn
    50                  55                  60

Lys Phe Thr Ile Ser Asn Cys
65                  70


<210> SEQ ID NO 120
<211> LENGTH: 71
<212> TYPE: PRT
<213> ORGANISM: Artificial Sequence
<220> FEATURE:
<223> OTHER INFORMATION: Ehrlichia antigenic peptide

<400> SEQUENCE: 120

Ser Ala Lys Glu Glu Lys Gln Thr Thr Thr Gly Leu Tyr Gly Leu Lys
1               5                   10                  15

Gln Asp Trp Asp Gly Ser Ala Ala Thr Ser Gly Gly Gly Gly Gly Asn
            20                  25                  30

Phe Ser Ala Lys Glu Glu Lys Ala Asp Thr Arg Lys Thr Phe Gly Val
        35                  40                  45

Glu Lys Gln Tyr Asp Gly Ala Lys Ile Ser Glu Asn Gln Val Gln Asn
    50                  55                  60

Lys Phe Thr Ile Ser Asn Cys
65                  70
```

COMPOSITIONS AND METHODS FOR IDENTIFYING *EHRLICHIA* SPECIES

CROSS-REFERENCE TO RELATED APPLICATIONS

This application is a continuation of U.S. application Ser. No. 15/226,108, filed Aug. 2, 2016, which is a continuation of U.S. application Ser. No. 14/252,696, filed Apr. 14, 2014, which claims the benefit of U.S. Provisional Application No. 61/975,581, filed Apr. 4, 2014, which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ABAX_043_03US_SeqList_ST25, date recorded Nov. 8, 2017, file size 85.3 kilobytes).

FIELD OF THE INVENTION

The present invention relates generally to compositions and methods for detecting bacterial infection and identifying bacteria species. In particular, the invention relates to peptide compositions, methods, and kits for detecting antibodies against bacterial antigens (e.g. antigens from *Ehrlichia* spp.).

BACKGROUND OF THE INVENTION

*Ehrlichia* bacteria are obligate intracellular pathogens that infect circulating lymphocytes in mammalian hosts. The most natural mode of *Ehrlichia* transmission is via a variety of tick vectors. *Ehrlichia canis* (*E. canis*) and *Ehrlichia chaffeensis* (*E. chaffeensis*) are members of the same subgenus group of *Ehrlichia* that infect canines and humans and cause canine monocytic ehrlichiosis (CME) and human monocytic ehrlichiosis (HME), respectively. Another species of *Ehrlichia* known as *Ehrlichia ewingii* (*E. ewingii*) has tropism for granulocytes and causes granulocytic ehrlichiosis. The canine disease is characterized by fever, epilepsy, incoordination, lethargy, bleeding episodes, lymphadenopathy, weight loss, and pancytopenia. In humans the disease is characterized by fever, headache, myalgia, and leukopenia.

Indirect immunofluorescence assays (IFA) and enzyme-linked immunosorbent assays (ELISA) have typically been used in the diagnosis of these diseases. These assays measure or otherwise detect the binding of anti-*Ehrlichia* antibodies from a subject's blood, plasma, or serum to infected cells, cell lysates, or partially purified whole *Ehrlichia* proteins. However, currently known assays for detecting anti-*Ehrlichia* antibodies or fragments thereof are severely limited in usefulness because of sensitivity and specificity issues directly related to the impure nature of the *Ehrlichia* antigen(s) used in these tests.

The diseases caused by bacteria belonging to different *Ehrlichia* species manifest differently and require separate management routine (Thomas, R. J., et al.; Expert Rev Anti Infect Ther. 2009 August; 7(6): 709-722). It is, therefore, important to identify the *Ehrlichia* species that causes a particular infection. The currently known immunoassays use mixtures of many whole *Ehrlichia* antigens or antigens that are not species specific. PCR methods, which may be useful to identify *Ehrlichia* species, are useable only if the tick is recovered and/or the tissue from host is tested soon after infection. Furthermore, cultivation of bacteria from the infection site, another method which may be useful to identify *Ehrlichia* species, is not only technically complex but also requires freshly infected tissue. In addition, a cultivation method for the species *E. ewingii* has not yet been developed.

Accordingly, there remains a need in the art for additional assays for detecting *Ehrlichia* antigens and serodiagnosis of monocytic ehrlichiosis and granulocytic ehrlichiosis. In particular, there remains a need for an assay for identifying *Ehrlichia* species, especially an assay that can be used in a variety of circumstances and for various samples, including samples that do not require isolation from freshly infected tissues. The present invention provides methods, compositions, and kits to facilitate the diagnosis, the species identification, and the treatment of the various types of *Ehrlichia* infections.

SUMMARY OF THE INVENTION

The present invention is based, in part, on the discovery that particular mixtures, or populations, of *Ehrlichia* peptides or their variants have preferential binding affinity for antibodies elicited by antigens from particular *Ehrlichia* species. The inventors have found that a particular combination of these peptide mixtures or populations can be used to identify the *Ehrlichia* species inducing the antibody response. Accordingly, the present invention provides a method for identifying the species of *Ehrlichia* infecting a subject.

In certain embodiments, the method for identifying the species of *Ehrlichia* infecting a subject comprises:

- contacting a sample from the subject with a first population of isolated peptides;
- detecting formation of a first set of complexes comprising an antibody and one or more peptides in the first population;
- contacting said sample with a second population of isolated peptides; and
- detecting formation of a second set of complexes comprising an antibody and one or more peptides in the second population, wherein formation of both the first and second sets of complexes indicates that the subject is infected with *E. ewingii*, and wherein formation of the first but not the second set of complexes indicates that the subject is infected with *E. canis* and/or *E. chaffeensis*. In some embodiments, the first population of isolated peptides comprises at least three different peptides, each comprising a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C (SEQ ID NO: 1) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid. In related embodiments, the second population of isolated peptides comprises at least three different peptides, each comprising a sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C (SEQ ID NO: 2) or a fragment thereof, wherein $X_7$ is any amino acid, $X_{12}$ is any amino acid, $X_{17}$ is any amino acid, $X_{24}$ is any amino acid, and $X_{26}$ is any amino acid In certain other embodiments, the method comprises:

contacting a sample from the subject with a first population of isolated peptides as described herein;

detecting formation of a first set of complexes comprising an antibody and one or more peptides in the first population;

contacting said sample with a third population of isolated peptides; and detecting formation of a third set of complexes comprising an antibody and one or more peptides in the third population, wherein formation of both the first and third sets of antibody-peptide complexes indicates that the subject is infected with *E. canis* and/or *E. chaffeensis*, and wherein formation of the first but not the third set of antibody-peptide complexes indicates that the subject is infected with *E. ewingii*. In certain embodiments, the third population of isolated peptides comprises at least three different peptides, each comprising a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid.

In certain embodiments, the method comprises:

contacting a sample from the subject with a first population of isolated peptides as described herein;

detecting formation of a first set of complexes comprising an antibody and one or more peptides in the first population;

contacting said sample with a second population of isolated peptides as described herein; detecting formation of a second set of complexes comprising an antibody and one or more peptides in the second population;

contacting said sample with a third population of isolated peptides as described herein; and detecting formation of a third set of complexes comprising an antibody and one or more peptides in the third population, wherein formation of both the first and second sets of complexes but not the third set indicates that the subject is infected with *E. ewingii*, and wherein formation of both the first and third sets of complexes but not the second set indicates that the subject is infected with *E. canis* and/or *E. chaffeensis*.

In some embodiments of the methods, one or more peptides in the first population of peptides comprises a fragment of SEQ ID NO: 1. The fragment of SEQ ID NO: 1 may comprise at least 20, 25, 30, 35, or 40 contiguous amino acids from SEQ ID NO: 1. In certain embodiments, the fragment of SEQ ID NO: 1 comprises amino acids 33 to 71 of SEQ ID NO: 1. In particular embodiments, each peptide in the first population comprises a sequence of SEQ ID NO: 1.

In certain other embodiments of the methods, one or more peptides in the second population of peptides comprises a fragment of SEQ ID NO: 2. The fragment of SEQ ID NO: 2 may comprise at least 15, 20, 25, 30, or 35 contiguous amino acids from SEQ ID NO: 2. In some embodiments, each peptide in the second population comprises a sequence of SEQ ID NO: 2.

In other embodiments of the methods, one or more peptides in the third population of peptides comprises a fragment of SEQ ID NO: 3. The fragment of SEQ ID NO: 3 may comprise at least 20, 25, 30, 35, or 40 contiguous amino acids from SEQ ID NO: 3. In certain embodiments, the fragment of SEQ ID NO: 3 comprises amino acids 33 to 71 of SEQ ID NO: 3. In particular embodiments, each peptide in the third population comprises a sequence of SEQ ID NO: 3.

In some embodiments of the methods, the sample is further analyzed with at least one assay to determine whether the infecting species is *E. canis* or *E. chaffeensis*.

In certain embodiments, at least one of the detecting steps in any of methods described herein may comprise: (i) performing an ELISA assay; (ii) running a lateral flow assay; (iii) performing an agglutination assay; (iv) performing a Western blot, slot blot, or dot blot assay; (v) performing a wavelength shift assay; (vi) running the sample through an analytical or centrifugal rotor; or (vii) running a microarray assay. In some embodiments, one or more of the detecting steps comprises spinning the sample in an analytical or centrifugal rotor. In other embodiments, one or more of the detecting steps comprises analyzing the sample with an electrochemical sensor, an optical sensor, chemiluminescence sensor or an opto-electronic sensor. In particular embodiments, one or more of the detecting steps comprises performing an ELISA assay or a lateral flow assay.

Certain embodiments of the method further comprise reporting detection results. The reporting can be done electronically, in writing, or verbally. It can be done via a machine such as a computer.

In another aspect, the invention provides kits for detecting antibodies that bind to *Ehrlichia* antigens and/or identifying the species of *Ehrlichia* infecting a subject. In certain embodiments, the kit comprises one, two, or three different populations of peptides of the invention as described herein. In certain embodiments, the kits further comprise an instruction for using the peptide populations to identify the species of *Ehrlichia* in a biological sample. In some embodiments, the kit further comprises one or more labeling reagents.

In certain embodiments of the methods or the kits of inventions, the peptides in the populations of isolated peptides are attached to or immobilized on a solid support.

Additional aspects and embodiments of the invention will be apparent from the detailed description that follows.

DETAILED DESCRIPTION

Figure 1:
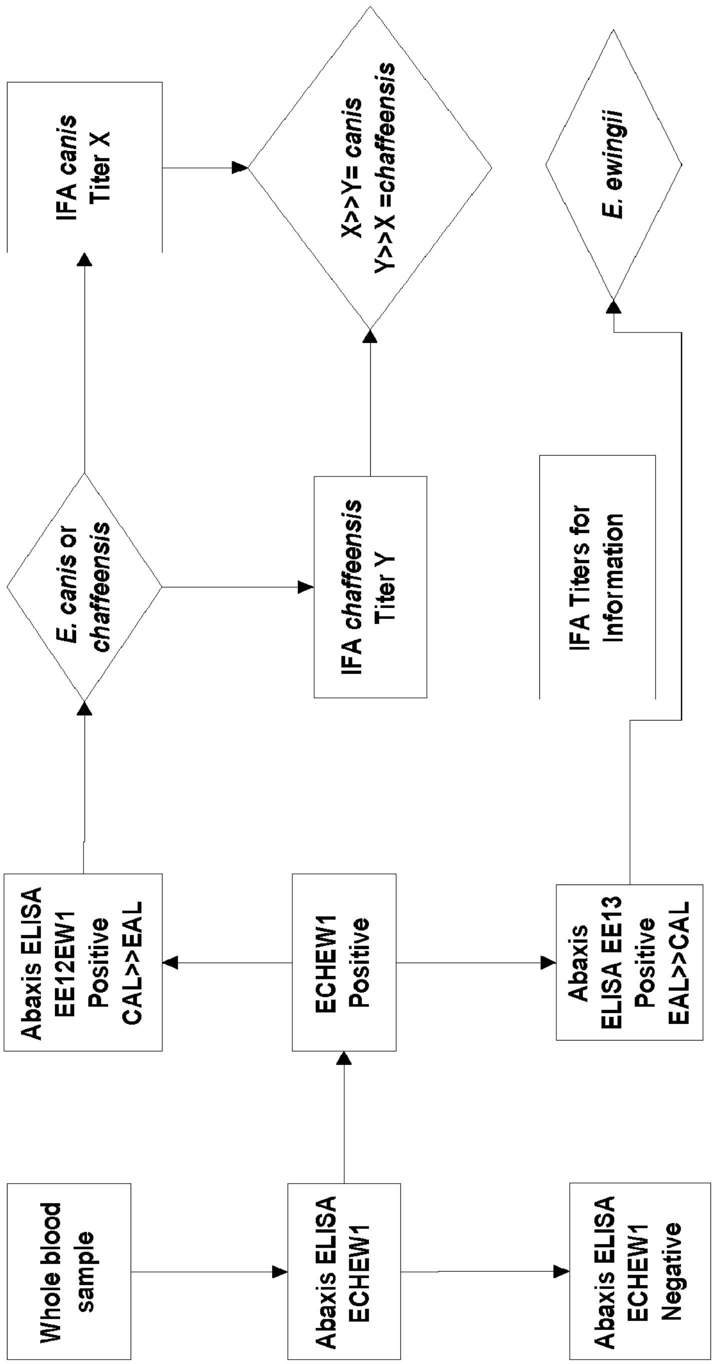
FIG. 1 is a diagram of an embodiment of a method for identifying *Ehrlichia* species. The abbreviation "EAL" represents ELISA score for an ELISA assay using peptide population EE13 (SEQ ID NO: 2), while "CAL" represents ELISA score for an ELISA assay using peptide population EE12EW1 (SEQ ID NO: 3). In this embodiment, a whole blood sample is tested in an ELISA assay, ELISA ECHEW1, using peptide population ECHEW1 (SEQ ID NO: 1), which comprises a first population of peptides as described herein. If the result of ELISA ECHEW1 is positive, the sample then undergoes another ELISA assay, ELISA EE13, using peptide population EE13, which comprises a second population of peptides as described herein, and undergoes yet another ELISA assay, ELISA EE12EW, using peptide population EE12EW, which comprises a third population of peptides as described herein. A positive result of ELISA EE13 combined with negative result of ELISA EE12EW, or a higher EAL than CAL, indicates that the sample is infected with *E. ewingii*. A positive result of ELISA EE12EW combined with negative result of ELISA EE13, or a higher CAL than EAL, indicates that the sample is infected with *E. canis* and/or *E. chaffeensis*. If the sample is identified to be infected with *E. canis* and/or *E. chaffeensis*, the sample then undergoes another assay, in this example an IFA assay for *E. canis* or *E. chaffeensis*, concurrently or non-concurrently, to determine whether the sample is infected with *E. canis* or *E. chaffeensis*.

As used herein, the following terms shall have the following meanings:

The term "antigen," as used herein, refers to a molecule capable of being recognized by an antibody. An antigen can be, for example, a peptide or a modified form thereof. An antigen can comprise one or more epitopes.

The term "epitope," as used herein, is a portion of an antigen that is specifically recognized by an antibody. An epitope, for example, can comprise or consist of a portion of a peptide (e.g., a peptide of the invention). An epitope can be a linear epitope, sequential epitope, or a conformational epitope. In certain embodiments, epitopes may comprise non-contiguous regions.

The term "OMP-1 protein" refers to any of the Outer Membrane Protein 1 paralogs of *Ehrlichia*, including, but not limited to, *E. canis* P-30, *E. canis* P30-1, *E. chaffeensis* P28, *E. chaffeensis* OMP-1C, *E. chaffeensis* OMP-1D, *E. chaffeensis* OMP-1E, and *E. chaffeensis* OMP-1F.

The term "MSP4 protein" refers to any member of the Surface Antigen MSP4 family of *Ehrlichia*, including, but not limited to, *E. canis* MSP4, P30-5, and P28-1. OMP and MSP are allelic variants.

The terms "nucleic acid," "oligonucleotide" and "polynucleotide" are used interchangeably herein and encompass DNA, RNA, cDNA, whether single stranded or double stranded, as well as chemical modifications thereof.

Single letter amino acid abbreviations used herein have their standard meaning in the art, and all peptide sequences described herein are written according to convention, with the N-terminal end to the left and the C-terminal end to the right.

The term "score" as used herein refers to a relative value, level, strength, or degree of an assay result. It can be artificially created by a person of skill in the art or by using an algorithm, sometimes using samples with known analytes, e.g., antigens or antibodies, optionally using samples with known concentrations or titers of the known analytes. It can be a number assigned manually by a person of skill in the art or generated with a formula or algorithm. It can also be a symbol, e.g., "–", "+", or "++". A score can be generated from calculation with a formula or algorithm, or can be assigned by visual inspection, measurement, or estimation of the assay result. When using samples with known concentrations or titers of known analytes, such samples can be assayed in diluted and undiluted conditions, and a range of scores or a standard curve of scores can be generated, which can be used to assign or estimate the scores of unknown samples assayed for the same analytes, preferably with the same assays.

Additional terms shall be defined, as required, in the detailed description that follows.

The present invention is based, in part, on the discovery that particular mixtures, or populations, of *Ehrlichia* peptides or their variants have preferential binding affinity for antibodies elicited by antigens from particular *Ehrlichia* species. The inventors have found that a particular combination of these peptide mixtures or populations can be used to identify the *Ehrlichia* species inducing the antibody response. Accordingly, the present invention provides a method for identifying the species of *Ehrlichia* infecting a subject, if present.

In certain embodiments, the method for identifying the species of *Ehrlichia* infecting a subject, if present, comprises:

contacting a sample from the subject with a first population of isolated peptides as described herein;

detecting formation of a first set of complexes comprising an antibody and one or more peptides in the first population;

contacting said sample with a second population of isolated peptides as described herein; and detecting formation of a second set of complexes comprising an antibody and one or more peptides in the second population, wherein formation of both the first and second sets of complexes indicates that the subject is infected with *E. ewingii*, and wherein formation of the first but not the second set of complexes indicates that the subject is infected with *E. canis* and/or *E. chaffeensis*.

In other embodiments, the method for identifying the species of *Ehrlichia* infecting a subject, if present, comprises:

- contacting a sample from the subject with a first population of isolated peptides as described herein;
- detecting formation of a first set of complexes comprising an antibody and one or more peptides in the first population;
- contacting said sample with a third population of isolated peptides as described herein; and
- detecting formation of a third set of complexes comprising an antibody and one or more peptides in the third population, wherein formation of both the first and third sets of antibody-peptide complexes indicates that the subject is infected with *E. canis* and/or *E. chaffeensis*, and wherein formation of the first but not the third set of antibody-peptide complexes indicates that the subject is infected with *E. ewingii*.

In yet other embodiments, the method for identifying the species of *Ehrlichia* infecting a subject, if present, comprises:

- contacting a sample from the subject with a first population of isolated peptides as described herein;
- detecting formation of a first set of complexes comprising an antibody and one or more peptides in the first population;
- contacting said sample with a second population of isolated peptides as described herein;
- detecting formation of a second set of complexes comprising an antibody and one or more peptides in the second population;
- contacting said sample with a third population of isolated peptides as described herein; and
- detecting formation of a third set of complexes comprising an antibody and one or more peptides in the third population, wherein formation of both the first and second sets of complexes but not the third set indicates that the subject is infected with *E. ewingii*, and wherein formation of both the first and third sets of complexes but not the second set indicates that the subject is infected with *E. canis* and/or *E. chaffeensis*.

In particular embodiments of the methods of the invention, the first population of isolated peptides is capable of specifically binding to antibodies against antigens from multiple species of *Ehrlichia*, including *E. canis, E. chaffeensis*, and *E. ewingii*. In certain embodiments, the first population of isolated peptides comprises at least three different peptides, each comprising a sequence S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C (SEQ ID NO: 1) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid.

In certain embodiments, $X_{39}$ in SEQ ID NO: 1 is K. In some embodiments, $X_{44}$ in SEQ ID NO: 1 is K or R, and/or $X_{49}$ in SEQ ID NO: 1 is E or D. In certain embodiments, $X_{56}$ in SEQ ID NO: 1 is K or Q, and/or $X_{58}$ in SEQ ID NO: 1 is E or T.

In certain other embodiments, the fragment of SEQ ID NO: 1 comprises at least 20, 25, 30, 35, or 40 contiguous amino acids from SEQ ID NO: 1. In certain embodiments, the fragment of SEQ ID NO: 1 comprises amino acids 33 to 71 of SEQ ID NO: 1. In particular embodiments, each peptide in the first population comprises a sequence of SEQ ID NO: 1.

In some embodiments, the first population of isolated peptides comprises at least one sequence, or a fragment thereof, selected from the group consisting of:

```
                                        (SEQ ID NO: 4)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

                                        (SEQ ID NO: 5)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-R-T-F-G-L-E-K-
Q-Y-D-G-A-K-I-E-E-N-Q-V-Q-N-K-F-T-I-S-N-C;

                                        (SEQ ID NO: 6)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-R-T-F-G-L-D-K-
Q-Y-D-G-A-K-I-E-E-N-Q-V-Q-N-K-F-T-I-S-N-C;

                                        (SEQ ID NO: 7)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-R-T-F-G-L-E-K-
Q-Y-D-G-A-Q-I-E-E-N-Q-V-Q-N-K-F-T-I-S-N-C;

                                        (SEQ ID NO: 8)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-K-T-F-G-L-D-K-
Q-Y-D-G-A-K-I-E-E-N-Q-V-Q-N-K-F-T-I-S-N-C;

                                        (SEQ ID NO: 9)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-K-T-F-G-L-D-K-
Q-Y-D-G-A-Q-I-E-E-N-Q-V-Q-N-K-F-T-I-S-N-C;

                                        (SEQ ID NO: 10)
S-A-K-E-E-K-Q-T-T-T-G-L-Y-G-L-K-Q-D-W-D-G-S-A-A-T-
S-G-G-G-G-G-N-F-S-A-K-E-E-K-A-E-T-R-K-T-F-G-L-E-K-
Q-Y-D-G-A-Q-I-E-E-N-Q-V-Q-N-K-F-T-I-S-N-C;
```

-continued (SEQ ID NO: 11)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-T-E-N-Q-V-Q-N-K-F-T-I-S-N-C;

(SEQ ID NO: 12)
S-V-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-T-E-N-Q-V-Q-N-K-F-T-I-S-N-C;

(SEQ ID NO: 13)
S-A-K-E-D-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-T-E-N-Q-V-Q-N-K-F-T-I-S-N-C;

(SEQ ID NO: 14)
S-V-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 15)
S-V-K-E-D-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 16)
S-A-K-E-D-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 17)
S-A-K-E-E-K-Q-P-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 18)
S-A-K-E-E-K-Q-P-T-T-A-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 19)
S-A-K-E-E-K-Q-P-T-T-G-V-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 20)
S-A-K-E-E-K-Q-T-T-T-A-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 21)
S-A-K-E-E-K-Q-T-T-T-A-V-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

-continued (SEQ ID NO: 22)
S-A-K-E-E-K-Q-T-T-T-G-V-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 23)
S-A-K-E-E-K-Q-T-T-T-G-L-F-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 24)
S-A-K-E-E-K-Q-T-T-T-G-L-F-G-L-K-Q-N-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 25)
S-A-K-E-E-K-Q-T-T-T-G-L-F-G-L-K-Q-D-W-N-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 26)
S-A-K-E-E-K-Q-T-T-T-G-L-Y-G-L-K-Q-N-W-D-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 27)
S-A-K-E-E-K-Q-T-T-T-G-L-Y-G-L-K-Q-N-W-N-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 28)
S-A-K-E-E-K-Q-T-T-T-G-L-Y-G-L-K-Q-D-W-N-G-S-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 29)
S-A-K-E-E-K-Q-T-T-T-G-L-Y-G-L-K-Q-D-W-D-G-V-A-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 30)
S-A-K-E-E-K-Q-T-T-T-G-L-Y-G-L-K-Q-D-W-D-G-V-S-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 31)
S-A-K-E-E-K-Q-T-T-T-G-L-Y-G-L-K-Q-D-W-D-G-V-T-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 32)
S-A-K-E-E-K-Q-T-T-T-G-L-Y-G-L-K-Q-D-W-D-G-S-S-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

-continued (SEQ ID NO: 33)
S-A-K-E-E-K-Q-T-T-T-G-L-Y-G-L-K-Q-D-W-D-G-S-T-A-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 34)
S-A-K-E-E-K-Q-T-T-T-G-L-Y-G-L-K-Q-D-W-D-G-S-S-I-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 35)
S-A-K-E-E-K-Q-T-T-T-G-L-Y-G-L-K-Q-D-W-D-G-S-T-I-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 36)
S-A-K-E-E-K-Q-T-T-T-G-L-Y-G-L-K-Q-D-W-D-G-S-A-I-T-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 37)
S-A-K-E-E-K-Q-T-T-T-G-L-Y-G-L-K-Q-D-W-D-G-S-A-A-P-
S-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 38)
S-A-K-E-E-K-Q-T-T-T-G-L-Y-G-L-K-Q-D-W-D-G-S-A-A-P-
N-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 39)
S-A-K-E-E-K-Q-T-T-T-G-L-Y-G-L-K-Q-D-W-D-G-S-A-A-P-
K-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 40)
S-A-K-E-E-K-Q-T-T-T-G-L-Y-G-L-K-Q-D-W-D-G-S-A-A-T-
N-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 41)
S-A-K-E-E-K-Q-T-T-T-G-L-Y-G-L-K-Q-D-W-D-G-S-A-A-T-
K-G-G-G-G-N-F-S-A-K-E-E-K-A-E-T-R-K-T-F-G-L-E-K-
Q-Y-D-G-A-K-I-E-E-N-Q-V-Q-N-K-F-T-I-S-N-C;

(SEQ ID NO: 42)
S-A-K-E-E-K-Q-T-T-T-G-L-Y-G-L-K-Q-D-W-D-G-S-A-A-T-
N-G-G-G-G-N-F-S-A-K-E-E-K-A-E-T-R-R-T-F-G-L-E-K-
Q-Y-D-G-A-K-I-E-E-N-Q-V-Q-N-K-F-T-I-S-N-C;

(SEQ ID NO: 43)
S-A-K-E-E-K-Q-T-T-T-G-L-Y-G-L-K-Q-D-W-D-G-S-A-A-T-
K-G-G-G-G-N-F-S-A-K-E-E-K-A-E-T-R-R-T-F-G-L-E-K-
Q-Y-D-G-A-K-I-E-E-N-Q-V-Q-N-K-F-T-I-S-N-C;

-continued (SEQ ID NO: 44)
S-A-K-E-E-K-Q-T-T-T-G-L-Y-G-L-K-Q-D-W-D-G-S-A-A-T-
S-G-G-G-G-N-F-S-A-K-E-E-R-A-E-T-R-K-T-F-G-L-E-K-
Q-Y-D-G-A-K-I-E-E-N-Q-V-Q-N-K-F-T-I-S-N-C;

(SEQ ID NO: 45)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-Q-T-F-G-L-E-K-
Q-Y-D-G-A-K-I-E-E-N-Q-V-Q-N-K-F-T-I-S-N-C;

(SEQ ID NO: 46)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-Q-K-
Q-Y-D-G-A-K-I-E-E-N-Q-V-Q-N-K-F-T-I-S-N-C;

(SEQ ID NO: 47)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-N-K-
Q-Y-D-G-A-K-I-E-E-N-Q-V-Q-N-K-F-T-I-S-N-C;

(SEQ ID NO: 48)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-R-I-E-E-N-Q-V-Q-N-K-F-T-I-S-N-C;

(SEQ ID NO: 49)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-E-I-E-E-N-Q-V-Q-N-K-F-T-I-S-N-C;

(SEQ ID NO: 50)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-D-E-N-Q-V-Q-N-K-F-T-I-S-N-C;
and (SEQ ID NO: 51)
S-A-K-E-E-K-Q-T-T-T-G-L-Y-G-L-K-Q-D-W-D-G-S-A-A-T-
S-G-G-G-G-N-F-S-A-K-E-E-K-A-E-T-R-K-T-F-G-L-E-K-
Q-Y-D-G-A-K-I-S-E-N-Q-V-Q-N-K-F-T-I-S-N-C.

In some embodiments, the first population of isolated peptides comprises at least two or three different sequences, or fragments thereof, selected from the group consisting of SEQ ID NOs: 4-51.

In particular embodiments of the methods, the second population of isolated peptides is capable of specifically or preferentially binding to antibodies against antigens from *E. ewingii*. In some embodiments, the second population of isolated peptides does not bind or minimally binds to antibodies against antigens from *E. canis* or *E. chaffeensis*. In certain embodiments, the second population of isolated peptides comprises at least three different peptides, each comprising a sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C (SEQ ID NO: 2) or a fragment thereof, wherein $X_7$ is any amino acid, $X_{12}$ is any amino acid, $X_{17}$ is any amino acid, $X_{24}$ is any amino acid, and $X_{26}$ is any amino acid.

In certain embodiments of the second population of isolated peptides, $X_7$ in SEQ ID NO: 2 is K. In some embodiments, $X_{12}$ in SEQ ID NO: 2 is K or R, and/or $X_{17}$ in SEQ ID NO: 2 is E or D. In certain embodiments, $X_{24}$ in SEQ ID NO: 2 is K or Q, and/or $X_{26}$ in SEQ ID NO: 2 is E or T.

In certain other embodiments, the fragment of SEQ ID NO: 2 comprises at least 15, 20, 25, 30, or 35 contiguous amino acids from SEQ ID NO: 2. In some embodiments, each peptide in the second population comprises a sequence of SEQ ID NO: 2.

In particular embodiments, the second population of isolated peptides comprises at least one sequence, or a fragment thereof, selected from the group consisting of:

(SEQ ID NO: 52)
F-S-A-K-E-E-K-A-E-T-R-K-T-F-G-L-E-K-Q-Y-D-G-A-K-I-

E-E-N-Q-V-Q-N-K-F-T-I-S-N-C;

(SEQ ID NO: 53)
F-S-A-K-E-E-K-A-E-T-R-R-T-F-G-L-E-K-Q-Y-D-G-A-K-I-

E-E-N-Q-V-Q-N-K-F-T-I-S-N-C;

(SEQ ID NO: 54)
F-S-A-K-E-E-K-A-E-T-R-R-T-F-G-L-E-K-Q-Y-D-G-A-Q-I-

E-E-N-Q-V-Q-N-K-F-T-I-S-N-C;

(SEQ ID NO: 55)
F-S-A-K-E-E-K-A-E-T-R-R-T-F-G-L-E-K-Q-Y-D-G-A-K-I-

T-E-N-Q-V-Q-N-K-F-T-I-S-N-C;

(SEQ ID NO: 56)
F-S-A-K-E-E-K-A-E-T-R-K-T-F-G-L-E-K-Q-Y-D-G-A-Q-I-

E-E-N-Q-V-Q-N-K-F-T-I-S-N-C;

(SEQ ID NO: 57)
F-S-A-K-E-E-K-A-E-T-R-K-T-F-G-L-E-K-Q-Y-D-G-A-Q-I-

T-E-N-Q-V-Q-N-K-F-T-I-S-N-C;

(SEQ ID NO: 58)
F-S-A-K-E-E-K-A-E-T-R-K-T-F-G-L-E-K-Q-Y-D-G-A-K-I-

T-E-N-Q-V-Q-N-K-F-T-I-S-N-C;

(SEQ ID NO: 59)
F-S-A-K-E-E-R-A-E-T-R-K-T-F-G-L-E-K-Q-Y-D-G-A-K-I-

E-E-N-Q-V-Q-N-K-F-T-I-S-N-C;

(SEQ ID NO: 60)
F-S-A-K-E-E-K-A-E-T-R-Q-T-F-G-L-E-K-Q-Y-D-G-A-K-I-

E-E-N-Q-V-Q-N-K-F-T-I-S-N-C;

(SEQ ID NO: 61)
F-S-A-K-E-E-K-A-E-T-R-K-T-F-G-L-Q-K-Q-Y-D-G-A-K-I-

E-E-N-Q-V-Q-N-K-F-T-I-S-N-C;

(SEQ ID NO: 62)
F-S-A-K-E-E-K-A-E-T-R-K-T-F-G-L-N-K-Q-Y-D-G-A-K-I-

E-E-N-Q-V-Q-N-K-F-T-I-S-N-C;

(SEQ ID NO: 63)
F-S-A-K-E-E-K-A-E-T-R-K-T-F-G-L-E-K-Q-Y-D-G-A-R-I-

E-E-N-Q-V-Q-N-K-F-T-I-S-N-C;

(SEQ ID NO: 64)
F-S-A-K-E-E-K-A-E-T-R-K-T-F-G-L-E-K-Q-Y-D-G-A-E-I-

E-E-N-Q-V-Q-N-K-F-T-I-S-N-C;

-continued (SEQ ID NO: 65)
F-S-A-K-E-E-K-A-E-T-R-K-T-F-G-L-E-K-Q-Y-D-G-A-K-I-

D-E-N-Q-V-Q-N-K-F-T-I-S-N-C;

and (SEQ ID NO: 66)
F-S-A-K-E-E-K-A-E-T-R-K-T-F-G-L-E-K-Q-Y-D-G-A-K-I-

S-E-N-Q-V-Q-N-K-F-T-I-S-N-C.

In some embodiments, the second population of isolated peptides comprises at least two or three different sequences, or fragments thereof, selected from the group consisting of SEQ ID NOs: 52-66.

In yet other embodiments of the method, the third population of isolated peptides is capable of specifically or preferentially binding to antibodies against antigens from *E. canis* and *E. chaffeensis*. In some embodiments, the third population of isolated peptides does not bind or minimally binds to antibodies against antigens from *E. ewingii*. In some embodiments, the third population of isolated peptides comprises at least three different peptides, each comprising a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid.

In certain embodiments of the third population of isolated peptides, $X_{39}$ in SEQ ID NO: 3 is K. In certain embodiments, $X_{44}$ in SEQ ID NO: 3 is K or R, and/or $X_{49}$ in SEQ ID NO: 3 is E or D. In certain embodiments, $X_{56}$ in SEQ ID NO: 3 is K or Q, and/or $X_{58}$ in SEQ ID NO: 3 is E or T.

In certain other embodiments, the fragment of SEQ ID NO: 3 comprises at least 20, 25, 30, 35, or 40 contiguous amino acids from SEQ ID NO: 3. In certain embodiments, the fragment of SEQ ID NO: 3 comprises amino acids 33 to 71 of SEQ ID NO: 3. In particular embodiments, each peptide in the third population comprises a sequence of SEQ ID NO: 3.

In particular embodiments, the third population of isolated peptides comprises at least one sequence, or a fragment thereof, selected from the group consisting of:

(SEQ ID NO: 67)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 68)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-R-T-F-G-V-E-K-Q-Y-D-G-A-K-I-E-E-N-Q-V-Q-N-K-F-T-I-S-N-C;

(SEQ ID NO: 69)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-R-T-F-G-V-D-K-Q-Y-D-G-A-K-I-E-E-N-Q-V-Q-N-K-F-T-I-S-N-C;

(SEQ ID NO: 70)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-R-T-F-G-V-E-K-Q-Y-D-G-A-Q-I-E-E-N-Q-V-Q-N-K-F-T-I-S-N-C;

(SEQ ID NO: 71)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-D-K-Q-Y-D-G-A-K-I-E-E-N-Q-V-Q-N-K-F-T-I-S-N-C;

(SEQ ID NO: 72)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-D-K-Q-Y-D-G-A-Q-I-E-E-N-Q-V-Q-N-K-F-T-I-S-N-C;

(SEQ ID NO: 73)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-Q-I-E-E-N-Q-V-Q-N-K-F-T-I-S-N-C;

(SEQ ID NO: 74)
S-A-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-T-E-N-Q-V-Q-N-K-F-T-I-S-N-C;

(SEQ ID NO: 75)
S-V-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-T-E-N-Q-V-Q-N-K-F-T-I-S-N-C;

(SEQ ID NO: 76)
S-A-K-E-D-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-T-E-N-Q-V-Q-N-K-F-T-I-S-N-C;

(SEQ ID NO: 77)
S-V-K-E-E-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 78)
S-V-K-E-D-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 79)
S-A-K-E-D-K-Q-T-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 80)
S-A-K-E-E-K-Q-P-T-T-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 81)
S-A-K-E-E-K-Q-P-T-V-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 82)
S-A-K-E-E-K-Q-P-T-T-A-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 83)
S-A-K-E-E-K-Q-T-T-V-G-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 84)
S-A-K-E-E-K-Q-T-T-V-A-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 85)
S-A-K-E-E-K-Q-T-T-A-L-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 86)
S-A-K-E-E-K-Q-T-T-T-G-V-Y-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 87)
S-A-K-E-E-K-Q-T-T-T-G-V-F-G-L-K-Q-D-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 88)
S-A-K-E-E-K-Q-T-T-T-G-V-Y-G-L-K-Q-N-W-D-G-S-A-A-T-S-G-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

-continued (SEQ ID NO: 89)
S-A-K-E-E-K-Q-T-T-T-G-L-F-G-L-K-Q-D-W-D-G-S-A-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 90)
S-A-K-E-E-K-Q-T-T-T-G-L-F-G-L-K-Q-N-W-D-G-S-A-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 91)
S-A-K-E-E-K-Q-T-T-T-G-L-Y-G-L-K-Q-N-W-D-G-S-A-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 92)
S-A-K-E-E-K-Q-T-T-T-G-L-Y-G-L-K-Q-D-W-N-G-S-A-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 93)
S-A-K-E-E-K-Q-T-T-T-G-L-Y-G-L-K-Q-D-W-N-G-S-S-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 94)
S-A-K-E-E-K-Q-T-T-T-G-L-Y-G-L-K-Q-D-W-N-G-S-T-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 95)
S-A-K-E-E-K-Q-T-T-T-G-L-Y-G-L-K-Q-D-W-D-G-V-A-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 96)
S-A-K-E-E-K-Q-T-T-T-G-L-Y-G-L-K-Q-D-W-D-G-V-S-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 97)
S-A-K-E-E-K-Q-T-T-T-G-L-Y-G-L-K-Q-D-W-D-G-V-T-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 98)
S-A-K-E-E-K-Q-T-T-T-G-L-Y-G-L-K-Q-D-W-D-G-S-S-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 99)
S-A-K-E-E-K-Q-T-T-T-G-L-Y-G-L-K-Q-D-W-D-G-S-T-A-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

-continued (SEQ ID NO: 100)
S-A-K-E-E-K-Q-T-T-T-G-L-Y-G-L-K-Q-D-W-D-G-S-A-I-T-N-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 101)
S-A-K-E-E-K-Q-T-T-T-G-L-Y-G-L-K-Q-D-W-D-G-S-A-I-T-K-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 102)
S-A-K-E-E-K-Q-T-T-T-G-L-Y-G-L-K-Q-D-W-D-G-S-A-I-T-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 103)
S-A-K-E-E-K-Q-T-T-T-G-L-Y-G-L-K-Q-D-W-D-G-S-A-A-P-S-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 104)
S-A-K-E-E-K-Q-T-T-T-G-L-Y-G-L-K-Q-D-W-D-G-S-A-A-P-N-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 105)
S-A-K-E-E-K-Q-T-T-T-G-L-Y-G-L-K-Q-D-W-D-G-S-A-A-P-K-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 106)
S-A-K-E-E-K-Q-T-T-T-G-L-Y-G-L-K-Q-D-W-D-G-S-A-A-T-N-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 107)
S-A-K-E-E-K-Q-T-T-T-G-L-Y-G-L-K-Q-D-W-D-G-S-A-A-T-K-G-G-G-G-N-F-S-A-K-E-E-K-A-D-T-R-K-T-F-G-V-E-K-Q-Y-D-G-A-K-I-E-E-N-Q-V-Q-N-K-F-T-I-S-N-C;

(SEQ ID NO: 108)
S-A-K-E-E-K-Q-T-T-T-G-L-Y-G-L-K-Q-D-W-D-G-S-A-A-T-S-G-G-G-G-N-F-S-A-K-E-E-K-A-N-T-R-K-T-F-G-V-E-K-Q-Y-D-G-A-K-I-E-E-N-Q-V-Q-N-K-F-T-I-S-N-C;

(SEQ ID NO: 109)
S-A-K-E-E-K-Q-T-T-T-G-L-Y-G-L-K-Q-D-W-D-G-S-A-A-T-S-G-G-G-G-N-F-S-A-K-E-E-K-A-N-T-R-K-T-F-G-A-E-K-Q-Y-D-G-A-K-I-E-E-N-Q-V-Q-N-K-F-T-I-S-N-C;

(SEQ ID NO: 110)
S-A-K-E-E-K-Q-T-T-T-G-L-Y-G-L-K-Q-D-W-D-G-S-A-A-T-S-G-G-G-G-N-F-S-A-K-E-E-K-A-N-T-R-K-T-F-G-V-D-K-Q-Y-D-G-A-K-I-E-E-N-Q-V-Q-N-K-F-T-I-S-N-C;

-continued (SEQ ID NO: 111)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-A-E-K-
Q-Y-D-G-A-K-I-E-E-N-Q-V-Q-N-K-F-T-I-S-N-C;

(SEQ ID NO: 112)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-A-D-K-
Q-Y-D-G-A-K-I-E-E-N-Q-V-Q-N-K-F-T-I-S-N-C;

(SEQ ID NO: 113)
S-A-K-E-E-K-Q-T-T-T-G-L-Y-G-L-K-Q-D-W-D-G-S-A-A-T-
S-G-G-G-G-N-F-S-A-K-E-E-R-A-D-T-R-K-T-F-G-V-E-K-
Q-Y-D-G-A-K-I-E-E-N-Q-V-Q-N-K-F-T-I-S-N-C;

(SEQ ID NO: 114)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-Q-T-F-G-V-E-K-
Q-Y-D-G-A-K-I-E-E-N-Q-V-Q-N-K-F-T-I-S-N-C;

(SEQ ID NO: 115)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-V-Q-K-
Q-Y-D-G-A-K-I-E-E-N-Q-V-Q-N-K-F-T-I-S-N-C;

(SEQ ID NO: 116)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-V-N-K-
Q-Y-D-G-A-K-I-E-E-N-Q-V-Q-N-K-F-T-I-S-N-C;

(SEQ ID NO: 117)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-V-E-K-
Q-Y-D-G-A-R-I-E-E-N-Q-V-Q-N-K-F-T-I-S-N-C;

(SEQ ID NO: 118)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-V-E-K-
Q-Y-D-G-A-E-I-E-E-N-Q-V-Q-N-K-F-T-I-S-N-C;

(SEQ ID NO: 119)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-V-E-K-
Q-Y-D-G-A-K-I-D-E-N-Q-V-Q-N-K-F-T-I-S-N-C;
and (SEQ ID NO: 120)
S-A-K-E-E-K-Q-T-T-T-G-L-Y-G-L-K-Q-D-W-D-G-S-A-A-T-
S-G-G-G-G-N-F-S-A-K-E-E-K-A-D-T-R-K-T-F-G-V-E-K-
Q-Y-D-G-A-K-I-S-E-N-Q-V-Q-N-K-F-T-I-S-N-C.

In some embodiments, the third population of isolated peptides comprises at least two or three different sequences, or fragments thereof, selected from the group consisting of SEQ ID NOs: 67-120.

In certain embodiments, the populations of isolated peptides used in the method comprise a fragment of a peptide sequence described herein. For example, in certain embodiments, the populations of isolated peptides comprise a fragment of a sequence selected from the group consisting of SEQ ID NOs: 1-120. The fragment can be, e.g., at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids in length. The fragment can be contiguous or can include one or more deletions (e.g., a deletion of 1, 2, 3, 4, 5, 6, 7, 8, 9, 10, or more amino acid residues). In some embodiments, the fragments comprise amino acids 1 to 26 of a sequence selected from the group consisting of SEQ ID NOs: 1-120. In other embodiments, the fragments comprise amino acids 33 to 71 of a sequence selected from the group consisting of SEQ ID NOs: 1, 3, 4-51, and 67-120. In certain embodiments, the fragments comprise an epitope of a peptide sequence selected from the group consisting of SEQ ID NOs: 1-120.

In some embodiments, one or more of the peptides in the first and/or third population of peptides used in the method are no longer than 71, 75, 80, 85, 90, 95, 100, 150, 200, 250, 300, 400, 500, 600, 700, 800, 900, 1000, 1200, 1500, or 2000 amino acids in length. In particular embodiments, at least three peptides in the first and/or third population of peptides are no longer than 71, 75, 80, 85, 90, 95, 100, 150, 200, 250, 300, 400, 500, 600, 700, 800, 900, 1000, 1200, 1500, or 2000 amino acids in length. In certain embodiments, each peptide in the first and/or third population of peptides is no longer than 71, 75, 80, 85, 90, 95, 100, 150, 200, 250, 300, 400, 500, 600, 700, 800, 900, 1000, 1200, 1500, or 2000 amino acids in length.

In some other embodiments, one or more of the peptides in the second population of peptides used in the method are no longer than 39, 40, 45, 50, 55, 60, 65, 70, 80, 90, 100, 150, 200, 250, 300, 400, 500, 600, 700, 800, 900, 1000, 1200, 1500, or 2000 amino acids in length. In particular embodiments, at least three peptides in the second population of peptides are no longer than 39, 40, 45, 50, 55, 60, 65, 70, 80, 90, 100, 150, 200, 250, 300, 400, 500, 600, 700, 800, 900, 1000, 1200, 1500, or 2000 amino acids in length. In certain embodiments, each peptide in the second population of peptides is no longer than 39, 40, 45, 50, 55, 60, 65, 70, 80, 90, 100, 150, 200, 250, 300, 400, 500, 600, 700, 800, 900, 1000, 1200, 1500, or 2000 amino acids in length.

In particular embodiments, each peptide in the first and third population of peptides is no longer than 71, 75, 80, 85, 90, 95, 100, 150, 200, 250, 300, 400, 500, 600, 700, 800, 900, 1000, 1200, 1500, or 2000 amino acids in length, and each peptide in the second population of peptides is no longer than 39, 40, 45, 50, 55, 60, 65, 70, 80, 90, 100, 150, 200, 250, 300, 400, 500, 600, 700, 800, 900, 1000, 1200, 1500, or 2000 amino acids in length.

In yet other embodiments, the populations of isolated peptides can comprise the peptides disclosed in U.S. application Ser. No. 14/052,296 and/or US Patent Application Publication No. 2011/0124125A1, the contents of which are hereby incorporated by reference in their entirety.

In some embodiments, the peptides in the populations of isolated peptides used in the method can comprise a sequence that is at least about 80, 85, 90, 95, 98, or 99% identical to a sequence selected from SEQ ID NOs: 1-120. Percent sequence identity has an art recognized meaning and there are a number of methods to measure identity between two polypeptide or polynucleotide sequences. See, e.g., Lesk, Ed., Computational Molecular Biology, Oxford University Press, New York, (1988); Smith, Ed., Biocomputing: Informatics And Genome Projects, Academic Press, New York, (1993); Griffin & Griffin, Eds., Computer Analysis Of Sequence Data, Part I, Humana Press, New Jersey, (1994); von Heinje, Sequence Analysis In Molecular Biology, Academic Press, (1987); and Gribskov & Devereux, Eds., Sequence Analysis Primer, M Stockton Press, New York, (1991). Methods for aligning polynucleotides or polypeptides are codified in computer programs, including the GCG program package (Devereux et al., Nuc. Acids Res. 12:387 (1984)), BLASTP, BLASTN, FASTA (Atschul et al., J Molec. Biol. 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (Adv. App. Math., 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polypeptide and that gaps in identity of up to 5% of the total number of amino acids in the reference polypeptide are allowed.

Variants of the peptide sequences can be readily selected by one of skill in the art, based in part on known properties of the sequence. For example, a variant peptide can include amino acid substitutions (e.g., conservative substitutions with naturally occurring amino acids, non-naturally occurring amino acids, or amino acid analogs) and/or deletions (e.g., small, single amino acid deletions, or deletions encompassing 2, 3, 4, 5, 10, 15, 20, or more contiguous amino acids). Thus, in certain embodiments, a variant of a native peptide sequence is one that differs from a naturally-occurring sequence by (i) one or more (e.g., 2, 3, 4, 5, 6, or more) conservative amino acid substitutions, (ii) deletion of 1 or more (e.g., 2, 3, 4, 5, 6, or more) amino acids, or (iii) a combination thereof. Deleted amino acids can be contiguous or non-contiguous. Conservative amino acid substitutions are those that take place within a family of amino acids that are related in their side chains and chemical properties. These include, e.g., (1) acidic amino acids: aspartate, glutamate; (2) basic amino acids: lysine, arginine, histidine; (3) nonpolar amino acids: alanine, valine, leucine, isoleucine, proline, phenylalanine, methionine, tryptophan; (4) uncharged polar amino acids: glycine, asparagine, glutamine, cysteine, serine, threonine, tyrosine; (5) aliphatic amino acids: glycine, alanine, valine, leucine, isoleucine, serine, threonine, with serine and threonine optionally grouped separately as aliphatic-hydroxyl; (6) aromatic amino acids: phenylalanine, tyrosine, tryptophan; (7) amide amino acids: asparagine, glutamine; and (9) sulfur-containing amino acids: cysteine and methionine. See, e.g., Biochemistry, 2nd ed., Ed. by L. Stryer, W H Freeman and Co.: 1981. Methods for confirming that variant peptides are suitable are conventional and routine.

Variants of the peptide sequences encompass variations on previously defined peptide sequences. For example, a previously described peptide sequence comprising a known epitope may be lengthened or shortened, at one or both ends (e.g., by about 1-3 amino acids), and/or one, two, three, four or more amino acids may be substituted by conservative amino acids, etc. Furthermore, if a region of a protein has been identified as containing an epitope of interest, an investigator can "shift" the region of interest (e.g., by about 5 amino acids in either direction) from the endpoints of the original rough region to optimize the activity.

In some embodiments, the peptides in the populations of isolated peptides used in the method can further comprise an additional N-terminal peptide sequence, an additional C-terminal peptide sequence, or a combination thereof.

In certain embodiments, the additional N-terminal peptide sequence can comprise 1, 2, 3, 4, 5, 6, 7, 8, 9, 10, or more amino acids and can be either a native or non-native sequence. In other embodiments, the additional C-terminal peptide sequence can comprise 1, 2, 3, 4, 5, 6, 7, 8, 9, 10, or more amino acids and can be either a native or non-native sequence.

The additional N-terminal or C-terminal peptide sequence can be a native sequence. As used herein, a "native" sequence is a peptide sequence from a naturally-occurring *Ehrlichia* OMP-1 sequence, or a variant thereof. In certain embodiments, the peptide sequence is a fragment of a naturally-occurring *Ehrlichia* OMP-1 sequence. The peptide sequence can be, e.g., from a conserved or non-conserved region of OMP-1. The peptide sequence can comprise, e.g., an epitope, such as an immunodominant epitope or any other epitope recognizable by a host (e.g., human, dog, etc.) immune system. OMP-1 proteins and peptides thereof have been described, e.g., in U.S. Pat. Nos. 6,544,517, 6,893,640, 6,923,963, 7,063,846, and 7,407,770, U.S. Patent Applications 2004/0265333 and 2009/0075368, and European Patent No. 1026949, the contents of each of which are incorporated herein by reference in their entirety.

In certain embodiments, the additional N-terminal or C-terminal peptide sequence is a non-native sequence. As used herein, a "non-native" sequence is any protein sequence, whether from an *Ehrlichia* protein or otherwise, other than a native OMP-1 peptide sequence.

In certain embodiments, the additional N-terminal or C-terminal peptide sequence can comprise or consist of another peptide having a sequence, or a fragment thereof, selected from SEQ ID NOs: 1-120.

In some embodiments, the additional N-terminal or C-terminal peptide sequence can be linked to the peptides in the populations of isolated peptides through one or more linking amino acids (e.g. glycine, serine, or cysteine residues).

The isolated peptides in the populations may be isolated by chemical synthesis and/or purification. In some embodiments, the peptides are produced biologically (i.e., by cellular machinery, such as a ribosome) and then isolated. As used herein, an "isolated" peptide is a peptide that has been produced either synthetically or biologically and then purified, at least partially, from the chemicals and/or cellular machinery used to produce the peptide. In certain embodiments, an isolated peptide of the invention is substantially purified. The term "substantially purified," as used herein, refers to a molecule, such as a peptide, that is substantially free of cellular material (proteins, lipids, carbohydrates, nucleic acids, etc.), culture medium, chemical precursors, chemicals used in synthesis of the peptide, or combinations thereof. A peptide that is substantially purified has less than about 40%, 30%, 25%, 20%, 15%, 10%, 5%, 2%, 1% or less of the cellular material, culture medium, other polypeptides, chemical precursors, and/or chemicals used in synthesis of the peptide. Accordingly, a substantially pure molecule, such as a peptide, can be at least about 60%, 70%, 75%, 80%, 85%, 90%, 95%, 98%, or 99%, by dry weight, the molecule of interest. An isolated peptide or population of peptides can be in water, a buffer, or in a dry form awaiting reconstitution, e.g., as part of a kit.

In certain embodiments, one or more peptides in the populations are conjugated to a ligand. For example, in certain embodiments, the peptides are biotinylated. In other embodiments, the peptides are conjugated to streptavidin, avidin, or neutravidin. In other embodiments, the peptides are conjugated to a carrier protein (e.g., serum albumin, keyhole limpet hemocyanin (KLH), or an immunoglobulin Fc domain). In still other embodiments, the peptides are conjugated to a dendrimer and/or are part of a multiple antigenic peptide system (MAPS). The peptides may also be conjugated to colloidal gold, quantum dots or other nanoparticles and/or to latex particles. In still another embodiment, the peptides may be conjugated to enzymes, fluorescent or chemi-luminescent markers.

In certain embodiments, peptides in the populations of isolated peptides are modified. The peptides of the invention may be modified by a variety of techniques, such as by denaturation with heat and/or a detergent (e.g., SDS). Alternatively, peptides of the invention may be modified by association with one or more further moieties. The association can be covalent or non-covalent, and can be, for example, via a terminal amino acid linker, such as lysine or cysteine, a chemical coupling agent, or a peptide bond. The additional moiety can be, for example, a ligand, a ligand receptor, a fusion partner, a detectable label, an enzyme, or a substrate that immobilizes the peptide.

In addition, the peptides in the populations of isolated peptides may be modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.

Modifications as set forth above are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins-Structure and Molecular Properties, 2nd ed., T. e. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

In certain embodiments, one or more or all peptides in a population of peptides is attached to or immobilized on a substrate, such as a solid or semi-solid support. The attachment can be covalent or non-covalent, and can be facilitated by a moiety associated with the peptide that enables covalent or non-covalent binding, such as a moiety that has a high affinity to a component attached to the carrier, support or surface. For example, the peptide can be associated with a ligand, such as biotin, and the component associated with the surface can be a corresponding ligand receptor, such as avidin. In some embodiments, the peptide can be associated with a fusion partner, e.g., bovine serum albumin (BSA), which facilitates the attachment of the peptide to a substrate. In other embodiments, the peptides of the invention are attached to or immobilized on a substrate via a metallic nanolayer such as a localized surface plasmon resonance spectroscopy (LSPR) surface. In one embodiment, the metallic nanolayer is comprised of cadmium, zinc, mercury, or a noble metal, such as gold, silver, copper, and platinum. The peptide or population of peptides can be attached to or immobilized on the substrate either prior to or after the addition of a sample containing antibody during an immunoassay.

In certain embodiments, the substrate is a bead, such as a colloidal particle (e.g., a colloidal nanoparticle made from gold, silver, platinum, copper, cadmium, metal composites, other soft metals, core-shell structure particles, or hollow gold nanospheres) or other type of particle (e.g., a magnetic bead or a particle or nanoparticle comprising silica, latex, polystyrene, polycarbonate, polyacrylate, or PVDF). Such particles can comprise a label (e.g., a colorimetric, chemiluminescent, or fluorescent label) and can be useful for visualizing the location of the peptides during immunoassays. In certain embodiments, a terminal cysteine of a peptide of the invention is used to bind the peptide directly to the nanoparticles made from gold, silver, platinum, copper, cadmium, metal composites, or other soft metals, or metallic nanoshells (e.g., gold hollow spheres, gold-coated silica nanoshells, and silica-coated gold shells).

In certain embodiments, the substrate is a dot blot or a flow path in a lateral flow immunoassay device. For example, the peptides can be attached or immobilized on a porous membrane, such as a PVDF membrane (e.g., an Immobilon™ membrane), a nitrocellulose membrane, polyethylene membrane, nylon membrane, or a similar type of membrane.

In certain embodiments, the substrate is a flow path in an analytical or centrifugal rotor. In other embodiments, the substrate is a tube or a well, such as a well in a plate (e.g., a microtiter plate) suitable for use in an ELISA assay. Such substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A substrate can be sintered, fine particles of polyethylene, commonly known as porous polyethylene, for example, 0.2-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one embodiment, the methods of invention involve detecting the presence of naturally occurring antibodies against one or more *Ehrlichia* antigens (e.g., the antigen of a pathogenic *Ehrlichia*, such as *E. chaffeensis, E. muris, E. ewingii*, or *E. canis*) which are produced by the infected subject's immune system in its biological fluids or tissues, and which are capable of binding specifically to one of more peptides in a population of peptides and, optionally, one or more suitable additional antigenic polypeptides or peptides.

For example, in one aspect, the present invention provides a method of detecting in a sample from a subject the presence of antibodies against antigens from *E. chaffeensis, E. muris, E. ewingii*, and/or *E. canis* comprising contacting the sample with a population of peptides comprising at least three different peptides, wherein each peptide comprises a sequence of SEQ ID NO: 1; and detecting formation of complexes comprising an antibody and one or more peptides in the population, wherein formation of the complexes indicates the presence of antibodies against antigens from *E. chaffeensis, E. muris, E. ewingii,* and/or *E. canis*. In some embodiments, the population of peptides comprises at least two or three different sequences selected from the group consisting of SEQ ID NOs: 4-51.

In other embodiments, the present invention provides a method of detecting in a sample from a subject the presence of antibodies against antigens from *E. ewingii* comprising contacting the sample with a population of peptides comprising at least three different peptides, wherein each peptide comprises a sequence of SEQ ID NO: 2; and detecting formation of complexes comprising an antibody and one or more peptides in the population, wherein formation of the complexes indicates the presence of antibodies against antigens from *E. ewingii*. In some embodiments, the population of peptides comprises at least two or three different sequences selected from the group consisting of SEQ ID NOs: 52-66.

In certain embodiments, the present invention provides a method of detecting in a sample from a subject the presence of antibodies against antigens from *E. chaffeensis* and/or *E. canis* comprising contacting the sample with a population of peptides comprising at least three different peptides, wherein each peptide comprises a sequence of SEQ ID NO: 3; and detecting formation of complexes comprising an antibody and one or more peptides in the population, wherein formation of the complexes indicates the presence of antibodies against antigens from *E. chaffeensis* and/or *E. canis*. In some embodiments, the population of peptides comprises at least two or three different sequences selected from the group consisting of SEQ ID NOs: 67-120.

There are a number of different assays that may be used to detect formation of antibody-peptide complexes comprising one or more peptides in the methods of the invention. For example, the detecting step can comprise performing an ELISA assay, performing an immunofluorescence assay, performing a lateral flow immunoassay, performing an agglutination assay, performing a wavelength shift assay, performing a Western blot, slot blot, or dot blot, analyzing the sample in an analytical or centrifugal rotor, or analyzing the sample with an electrochemical, optical, or opto-electronic sensor. These different assays are described herein and/or are well-known to those skilled in the art.

Suitable immunoassay methods typically include: receiving or obtaining (e.g., from a patient) a sample of body fluid or tissue likely to contain antibodies; contacting (e.g., incubating or reacting) a sample to be assayed with a population of peptides, under conditions effective for the formation of a specific peptide-antibody complex (e.g., for specific binding of the peptide to the antibody); and assaying the contacted (reacted) sample for the presence of an antibody-peptide reaction (e.g., determining the amount of an antibody-peptide complex). The presence of an elevated amount of the antibody-peptide complex indicates that the subject was exposed to and infected with an infectious *Ehrlichia* species. A peptide, including a modified form thereof, which "binds specifically" to (e.g., "is specific for" or binds "preferentially" to) an antibody against an *Ehrlichia* antigen interacts with the antibody, or forms or undergoes a physical association with it, in an amount and for a sufficient time to allow detection of the antibody. By "specifically" or "preferentially," it is meant that the peptide has a higher affinity (e.g., a higher degree of selectivity) for such an antibody than for other antibodies in a sample. For example, the peptide can have an affinity for the antibody of at least about 1.5-fold, 2-fold, 2.5-fold, 3-fold, or higher than for other antibodies in the sample. Such affinity or degree of specificity can be determined by a variety of routine procedures, including, e.g., competitive binding studies. In an ELISA assay, a positive response is defined as a value 2 or 3 standard deviations greater than the mean value of a group of healthy controls. In some embodiments, a second tier assay is required to provide an unequivocal serodiagnosis of monocytic and/or granulocytic ehrlichiosis.

Phrases such as "sample containing an antibody" or "detecting an antibody in a sample" are not meant to exclude samples or determinations (e.g., detection attempts) where no antibody is contained or detected. In a general sense, this invention involves assays to determine whether an antibody produced in response to infection with an infectious *Ehrlichia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc).

In some embodiments, the methods comprise receiving or obtaining a sample of body fluid or tissue likely to contain antibodies from a subject. The antibodies can be, e.g., of IgG, IgE, IgD, IgM, or IgA type. Generally, IgM and/or IgA antibodies are detected, e.g., for detection at early stages of infection. IgG antibodies can be detected when some of the additional peptides discussed above are used in the method (e.g., peptides for the detection of flagellum proteins). The sample is preferably easy to obtain and may be whole blood, plasma, or serum derived from a venous blood sample or even from a finger prick. Tissue from other body parts or other bodily fluids, such as cerebro-spinal fluid (CSF), saliva, gastric secretions, mucus, urine, etc., are known to contain antibodies and may be used as a source of the sample. The sample may also be a tissue extract or a cell lysate.

Once a population of peptides and sample antibody are permitted to react in a suitable medium, an assay is performed to determine the presence or absence of an antibody-peptide reaction. Among the many types of suitable assays, which will be evident to a skilled worker, are immunoprecipitation and agglutination assays performed with or without enhancement.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In certain embodiments, a peptide of the invention is immobilized on a solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices (e.g., lateral flow immunoassay devices), dipsticks, and immunocapillary or immunochromatographic immunoassay devices.

In some embodiments of the invention, the solid or semi-solid surface or carrier attached to the populations of peptides is the floor or wall in a microtiter well, a filter surface or membrane (e.g., a nitrocellulose membrane or a PVDF (polyvinylidene fluoride) membrane, such as an Immobilon™ membrane), a hollow fiber, a beaded chromatographic medium (e.g., an agarose or polyacrylamide gel), a magnetic bead, a fibrous cellulose matrix, an HPLC matrix, an FPLC matrix, a substance having molecules of such a size that the molecules with the peptide bound thereto, when dissolved or dispersed in a liquid phase, can be retained by means of a filter, a substance capable of forming micelles or participating in the formation of micelles allowing a liquid phase to be changed or exchanged without entraining the micelles, a water-soluble polymer, or any other suitable carrier, support or surface.

In some embodiments of the invention, a population of peptides is provided with a suitable label which enables detection. Conventional labels may be used which are capable, alone or in concert with other compositions or compounds, of providing a detectable signal. Suitable labels include, but are not limited to, enzymes (e.g., HRP, beta-galactosidase, alkaline phosphatase, etc.), fluorescent labels, radioactive labels, colored latex particles, and metal-conjugated labels (e.g., metallic nanolayers, metallic nanoparticle- or metallic nanoshell-conjugated labels). Suitable metallic nanoparticle or metallic nanoshell labels include, but are not limited to, gold particles, silver particles, copper particles, platinum particles, cadmium particles, composite particles, gold hollow spheres, gold-coated silica nanoshells, and silica-coated gold shells. Metallic nanolayers suitable for detectable layers include nanolayers comprised of cadmium, zinc, mercury, and noble metals, such as gold, silver, copper, and platinum.

Suitable detection methods include, e.g., detection of an agent which is tagged, directly or indirectly, with a colorimetric assay (e.g., for detection of HRP or beta-galactosidase activity), visual inspection using light microscopy, immunofluorescence microscopy, including confocal microscopy, or by flow cytometry (FACS), autoradiography (e.g., for detection of a radioactively labeled agent), electron microscopy, immunostaining, subcellular fractionation, or the like. In one embodiment, a radioactive element (e.g., a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody or other binding agent (e.g., protein A, protein G, protein L, chimeric proteins A/G, A/G/L, A/L, G/L or combinations thereof) which binds to the first antibody. This secondary antibody or other binding agent can be labeled, e.g., with a radioactive, enzymatic, fluorescent, luminescent, chemi-luminescent, metallic nanoparticle or metallic nanoshell (e.g. colloidal gold), or other detectable label, such as an avidin/biotin, avidin/streptavidin or avidin/polystreptavidin system. In another embodiment, the binding partner is a peptide of the invention, which can be conjugated directly or indirectly (e.g. via biotin/avidin or biotin/streptavidin interaction) to an enzyme, such as horseradish peroxidase or alkaline phosphatase or other signaling moiety. In such embodiments, the detectable signal is produced by adding a substrate of the enzyme that produces a detectable signal, such as a chromogenic, fluorogenic, or chemiluminescent substrate.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In some embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

A very useful assay format is a lateral flow immunoassay format. Antibodies to human or animal (e.g., dog, mouse, deer, etc.) immunoglobulins, or staph A, G, or L proteins, can be labeled with a signal generator or reporter (e.g., colloidal gold) that is dried and placed on a glass fiber pad (sample application pad or conjugate pad). The diagnostic peptide is immobilized on membrane, such as nitrocellulose or a PVDF (polyvinylidene fluoride) membrane (e.g., an Immobilon™ membrane). When a solution of sample (blood, serum, etc.) is applied to the sample application pad (or flows through the conjugate pad), it dissolves the labeled reporter, which then binds to all antibodies in the sample. The resulting complexes are then transported into the next membrane (PVDF or nitrocellulose containing the diagnostic peptide) by capillary action. If antibodies against the diagnostic peptide are present, they bind to the diagnostic peptide striped on the membrane, thereby generating a signal (e.g., a band that can be seen or visualized). An additional antibody specific to the labeled antibody or a second labeled antibody can be used to produce a control signal.

An alternative format for the lateral flow immunoassay comprises the populations of isolated peptides being conjugated to a ligand (e.g., biotin) and complexed with labeled ligand receptor (e.g., streptavidin-colloidal gold). The labeled peptide complexes can be placed on the sample application pad or conjugate pad. Anti-human IgG/IgM or anti-animal (e.g., dog, mouse, deer) IgG/IgM antibodies or other peptides of the invention are immobilized on a membrane, such as nitrocellulose of PVDF, at a test site (e.g., a test line). When a sample is added to the sample application pad, antibodies in the sample react with the labeled peptide complexes such that antibodies that bind to peptides of the invention become indirectly labeled. The antibodies in the sample are then transported into the next membrane (PVDF or nitrocellulose containing the diagnostic peptide) by capillary action and bind to the immobilized anti-human IgG/IgM or anti-animal IgG/IgM antibodies (or protein A, protein G, protein A/G fusion proteins, protein L, or combinations thereof) or immobilized peptides of the invention. If any of the sample antibodies are bound to the labeled peptides of the invention, the label associated with the peptides can be seen or visualized at the test site. In another embodiment of this type of lateral flow device (in which the peptides of the invention are used both as the immobilized capture agent at a test site and as a soluble labeled complex to react with antibodies in a sample), to amplify the detection signal, protein A, protein G, and/or protein A/G fusion proteins conjugated to a detectable label (e.g., metallic nanoparticle or nanoshell, HRP, ALP, fluorophore, colored latex particle) may be applied to the test site where they will bind to the Fc region of any antibodies to *Ehrlichia* antigens captured by the immobilized peptides of the invention. Suitable controls for this assay can include, e.g., a chicken IgY-colloidal gold conjugate located at the sample application pad or conjugate pad, and an anti-chicken IgY antibody immobilized at a control site located proximal to the test site. Other suitable controls can include chicken anti-Protein A, mouse IgG or any other proteins capable of binding to Protein A/G/L. In at least some of the lateral flow immunoassays performed in the methods of invention and described herein, chicken anti-Protein A was used as the control line.

Another assay for the screening of blood products or other physiological or biological fluids is an enzyme linked immunosorbent assay, i.e., an ELISA. Typically in an ELISA, isolated peptides or mixtures or populations of peptides are adsorbed directly, or following conjugation to a carrier protein, to the surface of a microtiter well directly or through a capture matrix (e.g., an antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-*Ehrlichia* (e.g., anti-*E. chaffeensis*, anti-*E. ewingii*, or anti-*E. canis*) antibody. Such biological sample can be a serum, plasma, or other type of sample. The sample can be applied neat, or more often it can be diluted, usually in a buffered solution which contains a small amount (0.1-10.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin (αHuIg) from another animal, such as dog, mouse, cow, etc.) or another peptide of the invention that is conjugated to an enzyme or other label by standard procedures and is dissolved in blocking buffer. The label can be chosen from a variety of enzymes, including horseradish peroxidase (HRP), beta-galactosidase, alkaline phosphatase (ALP), glucose oxidase, etc. In certain embodiments, Protein A or Protein G-HRP is used in the methods of invention. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD+3 standard deviations (SDs) of at least 50 serum samples collected from individuals from an area where ehrlichiosis is not endemic, or by other such conventional definitions. In the case of a very specific assay, OD+2 SD can be used as a cutoff value.

In another embodiment, the methods comprise an agglutination assay. For example, in certain embodiments, metallic nanoparticles or metallic nanoshells (e.g., colloidal gold, etc.) or latex beads are conjugated to the populations of isolated peptides. Subsequently, the biological fluid is incubated with the bead/peptide conjugate, thereby forming a reaction mixture. The reaction mixture is then analyzed to determine the presence of the antibodies. In certain embodiments, the agglutination assays comprise the use of a second population of particles, such as metallic nanoparticles or metallic nanoshells (e.g., colloidal gold, etc.) or latex beads, conjugated to (1) antibodies specific to the peptides of compositions of the invention, in the case of a competition assay, or (2) antibodies capable of detecting sample antibodies (e.g., anti-human IgG or IgM antibodies, anti-dog IgG or IgM antibodies, anti-cat IgG or IgM antibodies, etc.), in the case of a sandwich assay. Suitable agglutination methods can comprise centrifugation as a means of assessing the extent of agglutination.

In still other embodiments, the populations of isolated peptides are electro- or dot-blotted onto nitrocellulose paper. Subsequently, a sample, such as a biological fluid (e.g., serum or plasma) is incubated with the blotted antigen, and antibody in the biological fluid is allowed to bind to the antigen(s). The bound antibody can then be detected, e.g., by standard immunoenzymatic methods or by visualization using metallic nanoparticles or nanoshells coupled to secondary antibodies or other antibody binding agents, such as protein A, protein G, protein A/G fusion proteins, protein L, or combinations thereof.

In still other embodiments, peptide or compositions of the invention are electro- or dot-blotted onto nitrocellulose paper. Subsequently, a sample, such as a biological fluid (e.g., serum or plasma) is incubated with the blotted antigen, and antibody in the biological fluid is allowed to bind to the antigen(s). The bound antibody can then be detected, e.g., by standard immunoenzymatic methods or by visualization using metallic nanoparticles or nanoshells coupled to secondary antibodies or other antibody binding agents, such as protein A, protein G, protein A/G fusion proteins, protein L, or combinations thereof.

In still other embodiments, a protein microarray (or protein chip) is used in the methods. For example, in certain embodiments, the microarray or chip comprises a support surface such as a glass slide, nitrocellulose membrane, bead, or microtitre plate, which are conjugated to an array of capture proteins comprising a population of peptides as described above. Samples, optionally labeled with a fluorescent dye, are added to the array. Specific binding between the antibodies in the samples, if present, and the immobilized protein emits a fluorescent signal that is read by a laser scanner. Unlabeled antibodies bound to the peptides of invention may also be subsequently labeled with quantum dot-labeled Protein A, A/G, etc. Microarrays of isolated peptides may also be used in a microchip chip format in a centrifugal analyzer. Protein microarrays are high-throughput, rapid, automated, economical, and highly sensitive, consuming small quantities of samples and reagents.

It should be understood by one of skill in the art that any number of conventional protein assay formats, particularly immunoassay formats, may be designed to utilize the populations of isolated peptides for any of the methods described herein. This invention is thus not limited by the selection of the particular assay format, and is believed to encompass all suitable assay formats that are known to those of skill in the art.

Using any of the suitable assay formats described herein or otherwise known to those of skill in the art, formation of complexes comprising an antibody and one or more peptides in the populations of isolated peptides can be detected. By a “set” of complexes, it refers to complexes formed between one population of isolated peptides and any antibodies in a sample. When a detection result is described as formation of one but not another set of complexes, it includes a range of results that can be obtained with two different populations of isolated peptides. By “formation of the first but not the second set of complexes", e.g., it can include a clearly positive result obtained with the first population of isolated peptides and a clearly negative result with the second population of isolated peptides. It can also include a very high score of the result obtained with the first population of isolated peptides and a very low score of the result obtained with the second population of isolated peptides. It can further include any relatively higher score of the result obtained with the first population than the second population of isolated peptides.

For any of the assay formats described herein, a score can be assigned to the assay result of each sample. Such score refers to a relative value, level, strength, or degree of an assay result. It can be artificially created by a person of skill in the art or by using an algorithm, sometimes using samples with known analytes, e.g., antigens or antibodies, optionally using samples with known concentrations or titers of the known analytes (which can be called "standards" or "calibrators"). A score can be a number manually assigned by a person of skill in the art or generated with a formula or computer algorithm, e.g., from zero for a negative control to any positive number for a positive control (e.g., 1, 2, 3, 4, 5, 10, 20, 30, 40, 50, 60, 80, 100, 120, 150, 200, 300, 400, 500, 1000, etc.). It can also be represented by symbols, e.g., "−" for a negative control, and "+", "++", "+++", etc., for positive controls. A score can be determined by calculation with a formula or by automatic processing with a computer algorithm, or can be determined by visual inspection, measurement, or estimation of the assay result. When using samples with known concentrations or titers of known analytes (the standards or calibrators), such standards/calibrators can be assayed in diluted and undiluted conditions, and a range of scores or a standard curve of scores can be generated, which can be used to determine the scores of unknown samples assayed for the same analytes, preferably with the same assays and in the same assay runs.

In certain embodiments, the method uses a combination of immunochemical assays and three populations of peptides to identify whether a sample is infected with one, two or all three of the following *Ehrlichia* species: *E. canis, E. chaffeensis*, and *E. ewingii.*

In some embodiments of the method, a standard sample that has a known titer of antibodies against a certain species (e.g., *E. ewingii*), or a certain combination of species (e.g., *E. canis* and *E. chaffeensis*, or *E. canis, E. chaffeensis*, and *E. ewingii*) is tested. In certain embodiments, the standard sample is diluted to a series of standards/calibrators. Calibrators may be prepared using purified antibodies. Calibrators may also be prepared by selecting, pooling and/or diluting antisera/antibody samples with various levels of antibody titer. A person of skill in the art should know how to generate suitable calibrators. Scores and a standard curve can be generated for the series of standards/calibrator. In some embodiments, a cutoff is generated for a sample to be classified as positive for comprising antibodies against certain species of *Ehrlichia* (e.g., a cutoff for antibodies against *E. ewingii*, a cutoff for antibodies against *E. canis* and *E. chaffeensis*, and another cutoff for antibodies against *E. canis, E. chaffeensis*, and *E. ewingii*). A sample can be classified as a low, medium, or high sample. A low sample is usually just above the limit of detection, and a very high sample shows most response in a given population. Calibrators for ELISA are often prepared to represent the ranges from low to very high samples.

In certain embodiments, an unknown sample is tested with the same assays as the standards. In some embodiments, a score of the unknown sample is generated against the scores or the standard curve of each standard, e.g., a score of the unknown sample can be generated against a standard that has a known titer of antibodies against *E. ewingii*; and another score of the unknown sample can be generated against a standard that has a known titer of antibodies against both *E. canis* and *E. chaffeensis.*

Scores can be compared among samples assayed for a same analyte or for different analytes.

When comparing scores of samples assayed for a same analyte, the scores can be determined from and compared against the same range of scores or the same standard curve of scores generated from the standards/calibrators, if all the samples are assayed in the same experiment under the same conditions as the standards/calibrators. The scores can also be determined from different ranges of scores or different standard curves of scores from the standards/calibrators, if the samples are assayed in different experiments along with the same standards/calibrators. Then relative scores of the assayed samples in relation to the same standards/calibrators can be determined and compared to each other.

When comparing scores of samples assayed for different analytes, e.g., antibodies against different species of *Ehrlichia*, each species or combination of species (such as *E. canis* and *E. chaffeensis*) has its own calibrators. The limit of detection for each set of calibrators and assay is determined by generating a cutoff normally assigned by adding 2-3 standard deviations to the mean of the samples known to be negative for the antibodies being detected. The calibrators for the population of isolated peptides detecting all of the *Ehrlichia* species contain a mixture of antibodies to different *Ehrlichia* species in appropriate ratios, for example, at least 5% each of anti-*canis*, anti-*chaffeensis*, and anti-*ewingii*, so that there is enough of each species and the assay does not miss any of the assayed species. The calibrators for the population of peptides detecting both *E. canis* and *E. chaffeensis*, contain a mixture of anti-*canis* and anti-*chaffeensis* samples in appropriate ratios, for example, at least 5% of each species. The calibrators for the population of peptides detecting only *E. ewingii* contain only anti-*ewingii* samples. The calibrators for the population of peptides detecting *E. canis/E. chaffeensis* and for the population of peptides detecting *E. ewingii* are assigned the same range of scores which are limited to the linear portion of the respective standard curves.

In some embodiments, scores are generated from detecting the formation of complexes comprising antibodies and peptides in the populations of peptides as described herein. In certain embodiments, a score is generated from detecting the formation of complexes comprising antibodies in a sample, if present, and peptides in a first, second, or third population of peptides as described herein, resulting in a first score, a second score, or a third score, respectively.

In some embodiments, the second score is compared to the third score, manually or by using a computer. In particular embodiments, a sample is identified or classified to be infected with *E. ewingii* if the second score is higher than the third score. In other embodiments, a sample is identified or classified to be infected with *E. canis* and/or *E. chaffeensis* if the third score is higher than the second score.

In yet other embodiments, the method further comprises a step to determine whether the infecting species is *E. canis* or *E. chaffeensis*. For example in one such embodiment an assay is performed to detect antibodies against *E. canis* but not *E. chaffeensis*, to generate a score for *E. canis*. Another assay can be performed to detect antibodies against *E. chaffeensis* but *E. canis*, to generate a score for *E. chaffeensis*. The assay results, optionally the scores, are compared to each other to determine whether the infecting species is *E. canis* or *E. chaffeensis*. In some embodiments, if the score for *E. canis* is higher than the score for *E. chaffeensis*, the sample is classified as infected with *E. canis* but not *E. chaffeensis*. In other embodiments, if the score for *E. chaffeensis* is higher than the score for *E. canis*, the sample is classified as infected with *E. chaffeensis* but not *E. canis*. In some embodiments, if the two scores are identical, the sample is classified as infected with both *E. chaffeensis* and *E. canis* or as undetermined.

In certain embodiments, the sample used in the methods is from a wild animal (e.g., a deer or rodent, such as a mouse, chipmunk, squirrel, etc.). In other embodiments, the sample is from a lab animal (e.g., a mouse, rat, guinea pig, rabbit, monkey, primate, etc.). In other embodiments, the sample is from a domesticated or feral animal (e.g., a dog, a cat, a horse). In still other embodiments, the sample is from a human. In other embodiments, the sample is from a canine or feline subject. In some embodiments, the sample is a bodily fluid. In particular embodiments, the sample is a blood, serum, plasma, cerebral spinal fluid, mucus, urine, or saliva sample. In certain embodiments, the sample is a whole blood sample. In other embodiments, the sample is a tissue (e.g., a tissue homogenate), tissue extract, or a cell lysate.

Much of the preceding discussion is directed to the detection of antibodies against pathogenic *Ehrlichia*. However, it is to be understood that the discussion also applies to the detection of primed T-cells, either in vitro or in vivo.

It is expected that a cell-mediated immune response (e.g., a T-helper response) is generated, since IgG is produced. It is therefore expected that it will be possible to determine the immunological reactivity between primed T-cells and a population of peptides as described herein. In vitro this can be done by incubating T-cells isolated from the subject with the population of peptides and measuring the immunoreactivity, e.g., by measuring subsequent T-cell proliferation or by measuring release of cytokines from the T-cells, such as IFN-γ. These methods are well-known in the art.

When a method of the invention is carried out in vivo, any of a variety of conventional assays can be used. For example, one can perform an assay in the form of a skin test, e.g., by intradermally injecting, in the subject, a population of peptides as described herein. A positive skin reaction at the location of injection indicates that the subject has been exposed to and infected with the *Ehrlichia* species that the population of peptides is specific to. The species of *Ehrlichia* infecting the subject can be identified using the method of invention with the populations of peptides as described herein. This or other in vivo tests rely on the detection of a T-cell response in the subject.

Certain embodiments of the method further comprise reporting detection results. The reporting can be done electronically, in writing, or verbally. It can be done via a machine such as a computer.

In yet another aspect, the invention provides kits. In some embodiments, the kits comprise at least one population of isolated peptides as described herein. In particular embodiments, a kit comprises at least two or three different populations of peptides. In some embodiments, a kit comprises a first, second, and/or third populations of peptides as described herein. In certain embodiments, the kits further comprise an instruction.

In some embodiments, the kit is a kit for detecting antibodies that bind to *Ehrlichia* antigens and/or identifying the species of *Ehrlichia* infecting a subject, if present.

In certain embodiments, the kit comprises:

a first population of isolated peptides as described herein;

a second population of isolated peptides as described herein;

a third population of isolated peptides as described herein; and an instruction for using the first, second, and third populations of peptides to identify the species of *Ehrlichia* in a biological sample, if present.

In particular embodiments of the kits, the first population of isolated peptides is capable of specifically binding to antibodies against antigens from multiple species of *Ehrlichia* including *E. canis, E. chaffeensis*, and *E. ewingii*. In other embodiments, the first population of isolated peptides comprises at least three different peptides, each comprising a sequence of SEQ ID NO: 1 or a fragment thereof as described herein. Specific examples of the peptide sequences with SEQ ID NO: 1 that can be used in the kits have been described above, e.g., those with specific amino acids at locations that can have various amino acids. Some specific examples are SEQ ID NOs: 4-51. Fragments of SEQ ID NO: 1 that can be used in the kits have also been described above.

In other particular embodiments of the kits, the second population of isolated peptides is capable of specifically or preferentially binding to antibodies against antigens from *E. ewingii*, but not to or not preferentially to antibodies against antigens from *E. canis* or *E. chaffeensis*. In other embodiments, the second population of isolated peptides comprises at least three different peptides, each comprising a sequence of SEQ ID NO: 2 or a fragment thereof as described herein. Specific examples of the peptide sequences with SEQ ID NO: 2 that can be used in the kits have been described above, e.g., those with specific amino acids at locations that can have various amino acids. Some specific examples are SEQ ID NOs: 52-66. Fragments of SEQ ID NO: 2 that can be used in the kits have also been described above.

In yet other embodiments of the kits, the third population of isolated peptides is capable of specifically or preferentially binding to antibodies against antigens from *E. canis* and *E. chaffeensis*, but not to or not preferentially to antibodies against antigens from *E. ewingii*. In other embodiments, the third population of isolated peptides comprises at least two or three different peptides, each comprising a sequence of SEQ ID NO: 3 or a fragment thereof as described herein. Specific examples of the peptide sequences with SEQ ID NO: 3 that can be used in the kits have been described above, e.g., those with specific amino acids at locations that can have various amino acids. Some specific examples are SEQ ID NOs: 67-120. Fragments of SEQ ID NO: 3 that can be used in the kits have also been described above.

In certain embodiments of the kits, the peptide populations are attached to or immobilized on a solid support. In some embodiments, the peptide populations are attached to or immobilized on a solid support through a metallic nanolayer (e.g., cadmium, zinc, mercury, gold, silver, copper, or platinum nanolayer). In certain embodiments, the solid support is a bead (e.g., a colloidal particle or a metallic nanoparticle or nanoshell), a flow path in a lateral flow immunoassay device, a flow path in an analytical or centrifugal rotor, a tube or a well (e.g., in a plate), or a sensor (e.g., an electrochemical, optical, or onto-electronic sensor).

Reagents for particular types of assays can also be provided in kits of the invention. Thus, the kits can include a population of beads (e.g., suitable for an agglutination assay or a lateral flow assay), or a plate (e.g., a plate suitable for an ELISA assay). In other embodiments, the kits comprise a device, such as a lateral flow immunoassay device, an analytical or centrifugal rotor, a Western blot, a dot blot, a slot blot, or an electrochemical, optical, or opto-electronic sensor. The population of beads, the plate, and the devices are useful for performing an immunoassay. For example, they can be useful for detecting formation of an antibody-peptide complex comprising an antibody from a sample and a peptide of the invention. In certain embodiments, a peptide, a mixture of different peptides (i.e. population of peptides) of the invention, or a peptide composition of the invention is attached to or immobilized on the beads, the plate, or the device.

In addition, the kits can include various diluents and buffers, labeled conjugates or other agents for the detection of specifically bound antigens or antibodies (e.g. labeling reagents), and other signal-generating reagents, such as enzyme substrates, cofactors and chromogens. In some embodiments, the kit comprises an anti-human, anti-canine, or anti-feline IgG/IgM antibody conjugated to a detectable label (e.g., a metallic nanoparticle, metallic nanoshell, metallic nanolayer, fluorophore, quantum dot, colored latex particle, or enzyme) as a labeling reagent. In other embodiments, the kit comprises protein A, protein G, protein A/G fusion proteins, protein L, or combinations thereof conjugated to a detectable label (e.g., a metallic nanoparticle, metallic nanoshell, metallic nanolayer, fluorophore, colored latex particle, or enzyme) as a labeling reagent. An exemplary protein A/G fusion protein combines four Fc-binding domains from protein A with two from protein G. See, e.g., Sikkema, J. W. D., Amer. Biotech. Lab, 7:42, 1989 and Eliasson et al., J. Biol. Chem. 263, 4323-4327, 1988, both which are hereby incorporated by reference in their entireties.

Other components of a kit can easily be determined by one of skill in the art. Such components may include coating reagents, polyclonal or monoclonal capture antibodies specific for a population of peptides as described herein, purified or semi-purified extracts of these antigens as standards, monoclonal antibody detector antibodies, an anti-mouse, anti-dog, anti-cat, anti-chicken, or anti-human antibody conjugated to a detectable label, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex.

In certain embodiments, the kits comprise an instruction indicating how to use the first, second, and/or third populations of isolated peptides as described herein to detect an antibody to an *Ehrlichia* antigen and/or to identify the species of *Ehrlichia* infecting a subject, if present. In certain embodiments, the kits comprise an instruction indicating how to use a population of beads, a plate, or a device (e.g., comprising a peptide or a population of peptides of the invention) to detect an antibody to one or more *Ehrlichia* antigens and/or to identify the species of *Ehrlichia*. In particular embodiments, the instruction comprises directions to identify the species of *Ehrlichia* infecting a subject, if present, according to the methods described herein. In certain embodiments, the instruction comprises directions to contact a biological sample with the first, second, and third populations of peptides separately. In particular embodiments, the instruction comprises directions to contact a biological sample with the first, second, and third populations of peptides sequentially.

Such kits provide a convenient, efficient way for a clinical laboratory to diagnose infection by a pathogenic *Ehrlichia* and/or identifying the species of *Ehrlichia* infecting a subject.

In another aspect, the invention provides compositions useful for identifying the species of *Ehrlichia* infecting a subject, if present. In some embodiments, the composition comprises at least one population of isolated peptides as described herein. In certain embodiments, the invention provides a combination of compositions comprising the first, second, and third populations of peptides, respectively.

In another aspect, the invention provides devices useful for identifying the species of *Ehrlichia* infecting a subject, if present. In some embodiments, the device comprises at least one population of isolated peptides as defined above. In certain embodiments, the device comprises the first, second, and third populations of peptides.

In certain embodiments, the devices are useful for performing an immunoassay. For example, in certain embodiments, the device is a lateral flow immunoassay device. In some embodiments, the device is a slide comprised of a plurality of beads to which a peptide or population of peptides is attached. In other embodiments, the device is an analytical or centrifugal rotor. In other embodiments, the device is a dot blot, slot blot, or Western blot. In other embodiments, the device is a tube or a well, e.g., in a plate suitable for an ELISA assay. In still other embodiments, the device is an electrochemical sensor, an optical sensor, an opto-electronic sensor, an X-ray film, chemi-luminescence imager or a photon detection equipment.

The methods, kits, compositions, and devices of the invention offer a number of advantages. For example, they allow for simple, inexpensive, rapid, sensitive and accurate detection of antibodies against *Ehrlichia* and identification of the species of *Ehrlichia* infecting a subject, if present. They also avoid serologic cross-reactivity with other conditions with similar symptoms. This allows for an accurate diagnosis of the bacteria and species, thereby facilitates timely and appropriate treatment that may be needed for the particular species of *Ehrlichia*.

The following examples illustrate various aspects of the invention. The examples should, of course, be understood to be merely illustrative of only certain embodiments of the invention and not to constitute limitations upon the scope of the invention.

EXAMPLES

Example 1—Experimental Infection of does with *Ehrlichia* and Detection of Species-Specific Anti-*Ehrlichia* Antibodies with ELISA This example shows that antibodies specific to particular *Ehrlichia* species were generated and found reactive to the populations of peptides as described herein.

A number of dogs were experimentally infected with *E. canis, E. chaffeensis* or *E. ewingii* (four dogs for each *Ehrlichia* species) for the purpose of studying the course of pathological changes and antibody production. The animals were infected using cultures of *E. canis* and *E. chaffeensis*, respectively, and blood stabilates of *E. ewingii* (*E. ewingii* has not been successfully cultured, and thus no slides for conducting IFA are currently available for this species.) Plasma samples were drawn from the infected dogs at various time points to generated the “dog plasma samples”. Although all of the infected animals showed the presence of bacterial DNA by PCR, in the time period allowed for the study, only one of the *E. chaffeensis*-infected dogs and two of the *E. canis*-infected dogs showed the presence of anti-bacterial antibodies as determined by reactivity with SNAP 4DX Plus™ (manufactured by IDEXX Laboratories, Inc., which detects antibodies against *E. canis, E. ewingii* and *E. chaffeensis*). All the dog plasma samples from the infection study found positive on SNAP 4Dx Plus™ were also positive in the ELISA assays performed according to the method described below, using the first population of peptides as described below (ECHEW1).

Three different populations of peptides were synthesized using standard synthesis procedures. Each peptide in the first population of peptides (ECHEW1) contained a sequence of SEQ ID NO: 1, which comprises a chimeric peptide encompassing two different sequences that bind antibodies elicited to the following *Ehrlichia* antigens: msp4, p30 or p30-1 from *canis/chaffeensis* and 28 kD from *ewingii*. The ECHEW1 population of peptides specifically binds to antibodies elicited by multiple *Ehrlichia* spp. (*E. canis, E. chaffeensis*, and *E. ewingii*). Each peptide in the second population of peptides (EE13) contained a sequence of SEQ ID NO: 2. The EE13 population of peptides specifically binds to antibodies elicited primarily by *E. ewingii* with some low cross-reactivity to *E. canis* and *E. chaffeensis*. Each peptide in the third population of peptides (EE12EW1) contained a sequence of SEQ ID NO: 3. The EE12EW1 population of peptides specifically binds to antibodies elicited primarily by *E. canis* and *E. chaffeensis* with some low cross-reactivity to *E. ewingii*.

ELISA Method

1. Coating Antigen
    1.1. The desired number of wells in 96-well plates (Thermo Scientific Nunc™ MaxiSorp" Microplates) were coated with 1-20 µg/mL of Abaxis *Ehrlichia* antigen population ECHEW1, EE12EW1, or EE13, each conjugated to BSA and diluted in 0.1 M sodium carbonate/bicarbonate buffer (pH 9-9.4). Coating was performed by adding 0.1 mL of the antigen to each well and incubating the plate on a micro plate shaker at 250-300 rpm at room temperature for approximately one hour.
    1.2. The coating solution was removed, followed by dabbing the plates on paper towels to eliminate any hanging droplets. 0.3 mL of deionized water was added to each well, and the plates were shaken at 250-300 rpm for 5 minutes. The liquid was removed as above.
    1.3. The wash step as in 1.2 was repeated twice.
2. Blocking of the Plate
    2.1. The coated plate wells were blocked by treating with the blocking solution consisting of 30 g of non-fat milk in 100 mL of deionized water. Each well was filled with 0.3 ml of blocking solution and the plates were placed on a shaker at 250-300 rpm for approximately one hour.
    2.2. Blocking solution was removed and the plate was dabbed on a paper towel to remove hanging droplets.
3. Sample/Calibrator Incubation
    3.1 Anti-*Ehrlichia* antibody calibrators were generated from canine plasma by making a pool of high titer plasma samples against known species. Species was determined by SNAP 4DX Plus™ and SNAP 3DX™ (manufactured by IDEXX, which detects antibodies against *E. canis* and *E. chaffeensis*, but not *E. ewingii*) differential testings and IFA. The pool was then assigned an arbitrary score and diluted to various levels in a negative canine plasma diluent. The score scaled linearly with the dilution: for example, if a sample with score 40 was diluted 2 fold the resulting score would be 20. A set of five *Ehrlichia* calibrators was run on each plate for the *Ehrlichia* ELISA. One set was comprised of plasma samples that were positive to *E. canis, E. chaffeensis* and *E. ewingii*, and was used with an ECHEW1-coated plate. One set was comprised of anti-*E. canis/E. chaffeensis*-positive samples, using samples that show close titers in the IFA for *canis* and *chaffeensis*, respectively, and was used with an ECHEW1-coated plate and a EE12EW1-coated plate. Another set was comprised of anti-*E. ewingii*-positive samples and was used with a EE13-coated plate. Each dog plasma sample or calibrator was diluted 250-fold in the blocking solution. Aliquots of 0.1 mL of each of the diluted calibrators and the dog plasma samples were added to the wells and plates were placed on the shaker at 250-300 rpm for one hour. Both the calibrators and dog plasma samples were run in duplicate and the results reported are the average of the two readings.
    3.2. The sample solution was removed and the plate was washed in the washing buffer containing 50 mM Trizma base (Sigma-Aldrich T1503) and 0.05% CHAPS detergent (pH 8.0) (Sigma-Aldrich C3023). The washing step was carried out by adding 0.3 mL of the washing buffer and shaking the plate at 250-300 rpm for 5 minutes. The washing solution was removed by inverting the plate and then dabbing on a paper towel to eliminate any hanging droplets.
    3.3 The above washing step was repeated twice.
4. Conjugate Incubation
    4.1. Protein A-HRP conjugate (Bio-Rad 170-6522) was diluted 8000-fold in the blocking solution (described in 2.1 above) and 0.1 mL of the diluted conjugate was added to each well. The plates were then incubated with shaking at 250-300 rpm at room temperature for approximately one hour.
    4.2. The conjugate was removed and the plates were dabbed on a paper towel to remove hanging droplets. The plates were washed thrice as described above in 3.2 and 3.3. Finally, the plates were washed with 0.3 mL of distilled water per well.
    4.3. The bound conjugate was assayed by adding 0.1 mL of the substrate TMB solution (Millipore ES022). The substrate was allowed to react for 10 min at room temperature before OD 650 nm readings were taken on a plate reader (Spectramax 340 PC.).

Figure 2:
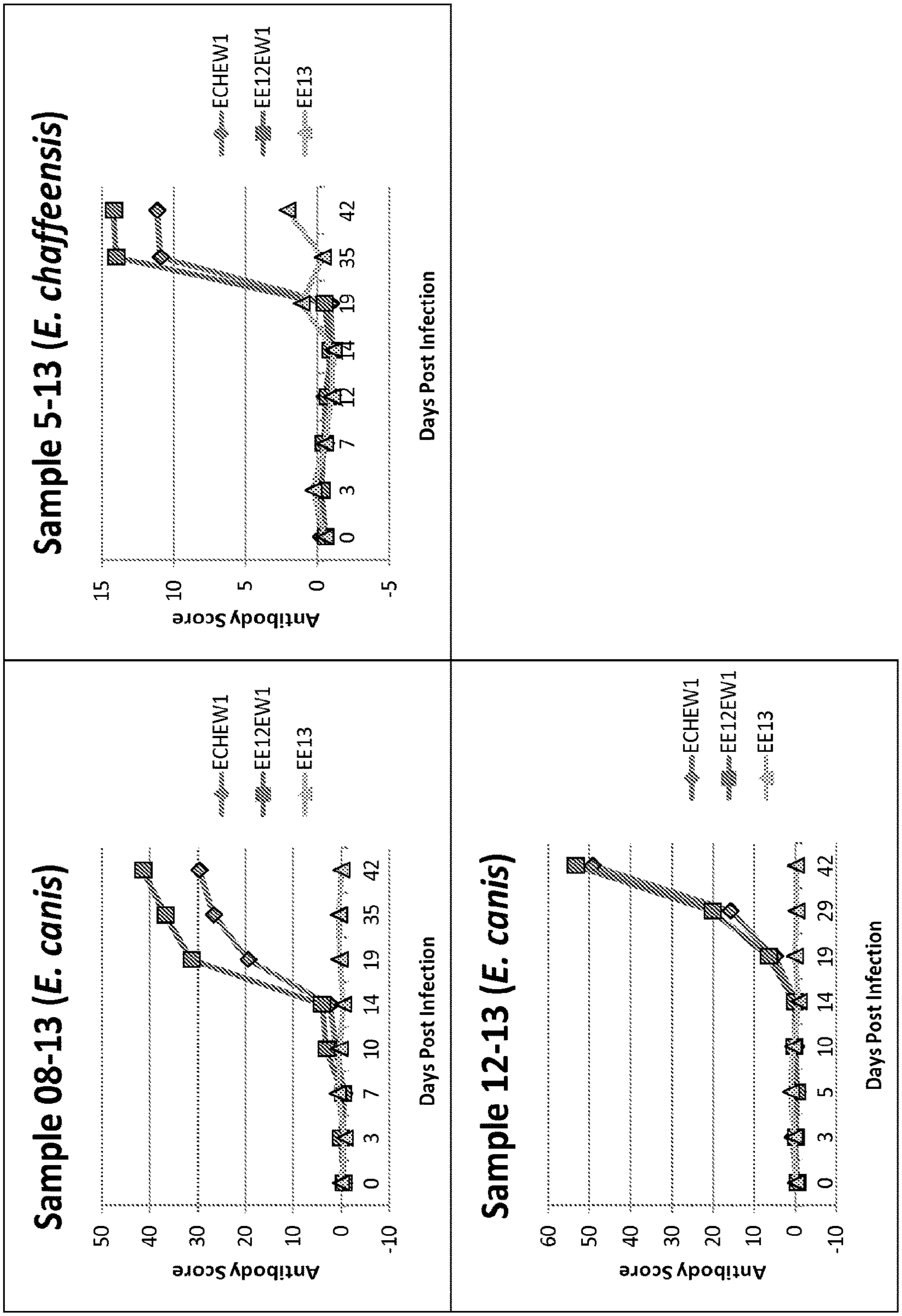
FIG. 2 is a graphical representation of anti-*Ehrlichia* antibody scores of plasma samples drawn at various times from dogs infected with the indicated *Ehrlichia* species. Dogs were experimentally infected with various species of *Ehrlichia*, and plasma samples were drawn on various days post infection as indicated in the graphs. ELISA assays were performed on the samples using each of the three populations of peptides, ECHEW1, EE12EW, and EE13. The top left and bottom left panels show the results from samples separately taken from two dogs infected with *E. canis*. The top right panel shows the results from samples taken from a dog infected with *E. chaffeensis*. Antibody scores were calculated using methods described herein.

Plasma samples from the infected dogs were drawn at several time points and assayed with the *Ehrlichia* ELISA method as described above using ECHEW1, EE13, and EE12EW1, respectively. The results are shown in FIG. 2. These results show the reactivity of ECHEW1 and EE12EW1 with antibodies produced in response to *E. canis* and *E. chaffeensis*. The antibodies produced in response to *E. canis* did not react with *E. ewingii*-specific peptide population EE13. A very slight cross-reactivity of the 42 day-post-infection sample from the *E. chaffeensis*-infected dogs with EE13 was noted.

Example 2—Detection of Presence of and Species-Specific Antibodies from Additional Known Anti-*Ehrlichia*-Positive or Negative Samples Using the Populations of Peptides This example shows the detection of the presence of anti-*Ehrlichia* antibodies and, if present, the species-specific antibodies from additional samples that were identified by reference methods to be anti-*Ehrlichia*-positive or negative, using the ECHEW1, EE13, and EE12EW1 populations of peptides in ELISA. It shows that the ELISA results agree with reference method results.

Each peptide in the three populations, ECHEW1, EE13, and EE12EW1, was linked separately to the carrier protein bovine serum albumin (BSA) using thio-ether chemistry. The resulting BSA-peptide conjugates were used as capture entities in 96-well ELISA plates to create three separate ELISA assays (one population of peptides per plate). The plates were then blocked to prevent undesirable non-specific binding.

A total of 224 anti-*Ehrlichia*-positive samples (dog plasma samples positive to *E. Canis, E. chaffeensis*, or *E. ewingii* as determined by IFA and SNAP 4DX Plus™/SNAP 3Dx™) and 264 anti-*Ehrlichia*-negative samples (244 dog plasma samples and 20 dog whole blood samples negative to E. *Canis, E. chaffeensis*, and *E. ewingii* as determined by the same reference methods) were incubated with the immobilized peptide populations in each of the three ELISA plates. After one hour incubation, the unreacted materials were removed by washing the micro wells. The specifically captured dog IgG or IgM were detected by reaction with HRP-labeled Protein A. HRP was assayed using a commercial TMB substrate. The optical density of each well was read at 650 nm with a plate reader. A summary of the results separated by "Sample Status", from IFA and SNAP tests, is shown in Table 1 below.

TABLE 1

ELISA Results of Known *Ehrlichia*-Positive or Negative Samples

| | ELISA Result[2] | | | |
|---|---|---|---|---|
| Sample Status[1] | ECHEW1-Positive with EE12EW1 > EE13 | ECHEW1-Positive with EE13 > EE12EW1 | ECHEW1-Negative | Total |
| *E. canis* | 50 | 0 | 1 | 51 |
| *E. chaffeensis* | 49 | 4 | 4 | 57 |
| *E. ewingii* | 2 | 80 | 10 | 92 |
| Positive, species indeterminate | 23 | 1 | 0 | 24 |
| Negative | 2 | 3 | 259 | 264 |

[1]The Sample Status was determined from the results of IFA and SNAP tests.

[2]An ELISA Result for ECHEW1 was classified as "positive" if it had a score ≥3 or "negative" if it had a score <3.

Of the 224 anti-*Ehrlichia*-positive samples (determined by IFA and SNAP tests), 209 were identified positive by our ELISA assay using the peptide population ECHEW1. Thus, the percent sensitivity of the ELISA ECHEW1 was 93.3%. Of the 264 anti-*Ehrlichia*-negative samples, 259 were identified negative by our ELISA assay. Thus, the percent specificity of the ELISA ECHEW1 was 98.1%. Furthermore, of the 108 samples that were classified as anti-*E. canis*-specific or anti-*E. chaffeensis*-specific by IFA and SNAP tests, 99 ("ECHEW1-Positive with EE12EW1> EE13") were correctly identified by our ELISA detection process. Of the 92 samples that were classified as anti-*E. ewingii*-specific by IFA and SNAP tests, 80 ("ECHEW1-Positive with EE13>EE12EW1") were identified by our ELISA detection process. Therefore, our ELISA methods are in good agreement with the reference methods.

In addition, of the 25 anti-*Ehrlichia*-positive samples whose species information could not be determined by IFA or SNAP assays, our ELISA identified them to be either *E. Canis/E. chaffeensis* specific (if the EE12EW1 score was greater than the EE13 score) or *E. ewingii* specific (if the EE13 score was greater than the EE12EW1 score), with fairly high confidence.

In some embodiments, lateral flow immunoassays can be used in place of the ELISA assays in methods described above. Therefore, other assay formats employing the populations of peptides as described herein can be used in the methods of the invention to identify *Ehrlichia* species.

Example 3—Generation of Standard Curves and Identification of Three Unknown Samples This example demonstrates in detail how standard curves for the three populations of isolated peptides, ECHEW1, EE13, and EE12EW1, could be generated, as well as how three unknown samples were classified according to the methods of the invention.

An ELISA assay was performed according to the method described in Example 1. In particular, a set of five *Ehrlichia* calibrators generated from known canine plasma samples as described in Example 1 was run on each plate for the *Ehrlichia* ELISA. One set was comprised of *E. canis/E. chaffeensis* positive samples and was used with an ECHEW1-coated plate and an EE12EW1-coated plate. Another set was comprised of *E. ewingii* positive samples and was used with an EE13-coated plate.

Each of three unknown canine plasma samples was diluted 250, 500 and 1000-fold in the blocking solution. Aliquots of 0.1 mL of each of the diluted calibrators and the unknown samples were then added to the wells and plates were placed on the shaker at 250-300 rpm for one hour.

Both the calibrators and unknown samples were run in duplicate and the results reported are the average of the two readings.

Data Analysis

A standard curve for each population of peptides was prepared by using the respective ELISA calibrators with scores (ECHEW1 Score for all species, EE12EW1 Score for *canis* and/or *chaffeensis*, and EE13 Score for *ewingii*) on the x-axis and optical density (OD) on the y axis. The *Ehrlichia* scores of the unknown samples were interpolated from this standard curve. The ECHEW1 Score, EE12EW1 Score, or EE13 Score for an unknown sample was determined by using the OD from a dilution that falls within the calibration curve.

Results

The ELISA results (OD 650 nm readings) of the calibrators are shown in Table 2:

TABLE 2

Standard Curves (Assigned Scores and OD Readings of Calibrators)

| Score | OD 650 nm ECHEW1 | OD 650 nm EE12EW1 | OD 650 nm EE13 |
|---|---|---|---|
| 0 | 0.00 | 0.00 | 0.00 |
| 10 | 0.04 | 0.03 | 0.06 |
| 40 | 0.40 | 0.24 | 0.13 |
| 80 | 0.72 | 0.43 | 0.28 |
| 120 | 1.03 | 0.68 | 0.83 |

Standard curves were calculated as follows:

ECHEW1: OD=0.0088 (ECHEW1 Score)+0.0027

EE12EW1: OD=0.0055 (EE12EW1 Score)+0.005

EE13: OD=0.0069 (EE13 Score)+0.0029

The ELISA results of the unknown samples are shown in Table 3:

TABLE 3

| ELISA OD Readings of Unknown Samples | | | |
|---|---|---|---|
| Sample Name | OD 650 nm ECHEW1 | OD 650 nm EE12EW1 | OD 650 nm EE13 |
| Unknown 1 | 0.42 | 0.03 | 0.34 |
| Unknown 2 | 0.48 | 0.31 | 0.01 |
| Unknown 3 | 0.0003 | 0.012 | 0.002 |

Scores of the unknown samples were calculated by the following formula:

$$(\text{SCORE})=(\text{OD}-B)/A$$

Where B is the intercept of the standard curve and A is the slope.

For each score the OD and the constants used come from the peptide population in question.

The scores calculated for each unknown sample are as follows:

1.) Unknown 1

(ECHEW1 Score)=(0.42−0.0027)/0.0088=47

(EE12EW1 Score)=(0.03−0.005)/0.0055=5

(EE13 Score)=(0 0.34−0.0029)/0.0069=49

The ECHEW1 Score was used to determine if the sample is positive or negative for infection with any species from *E. canis, E. chaffeensis*, and *E. ewingii*. Then the EE13 Score was compared to the EE12EW1 Score to determine the species of the infection. In this case, for Unknown 1, ECHEW1 Score is positive, and EE13 Score >>EE12EW1 Score, so the sample is positive for *E. ewingii.*

2.) Unknown 2

(ECHEW1 Score)=(0.48−0.0027)/0.0088=54

(EE12EW1 Score)=(0.31−0.005)/0.0055=55

(EE13 Score)=(0.01−0.0029)/0.0069=1

EE12EW1 Score >>EE13 Score, so the sample is positive for *E. canis/E. chaffeensis.*

3.) Unknown 3

(ECHEW1 Score)=(0.003−0.0027)/0.0088=0

(EE12EW1 Score)=(0.012−0.005)/0.0055=1

(EE13 Score)=(0.002−0.0029)/0.0069=0

All three scores are very low so the sample is negative for all three *Ehrlichia* species.

Cutoff

The cutoff for the ELISA test method was calculated on the basis of analysis of 294 samples, 128 negatives and 166 positives. These samples were classified by use of SNAP 4Dx Plus and E. *Canis* and E. *Chaffeensis* IFA titers. The samples used in this study were any for which both methods agreed, i.e., both SNAP and IFA were Positive or both were Negative. In this case whichever IFA titer was higher was the value used. Each of these 294 samples was tested using ELISA assays according to the procedure described in Example 1, and an antibody level score was assigned to each assay result for each sample. Positive and negative status for a sample run through this ELISA assay were determined on the basis of ECHEW1 Score alone so all the calculations here were concerning the ECHEW1 score for these samples.

The cutoff was set at three standard deviations above the negative mean. For this sample set that is:

Mean of Negative samples 0.37

Standard Deviation of Negative samples 0.82

Mean+3×{StDev}2.84

In this Example all scores were rounded to the nearest integer so any sample with an ECHEW1 Score >=3 were considered a positive. At an ELISA score of 3, one would expect 99.2% Specificity and 95.8% Sensitivity.

To the extent that any definitions in documents incorporated by reference are inconsistent with the definitions provided herein, the definitions provided herein are controlling. Although the invention has been described with reference to the presently preferred embodiments, it should be understood that various changes and modifications, as would be obvious to one skilled in the art, can be made without departing from the spirit of the invention. Accordingly, the invention is limited only by the following claims.

The disclosures, including the claims, figures and/or drawings, of each and every patent, patent application, and publication cited herein are hereby incorporated herein by reference in their entireties.

What is claimed is:

1. A method for identifying the species of *Ehrlichia* infecting a subject, if present, the method comprising:

contacting a sample from the subject with a first population of isolated peptides comprising at least three different peptides, each comprising a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-E-T-R-$X_{44}$-T-F-G-L-$X_{49}$-K-Q-Y-D-G-A-$X_{56}$-I-$X_{58}$-E-N-Q-V-Q-N-K-F-T-I-S-N-C (SEQ ID NO: 1) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{44}$ is any amino acid, $X_{49}$ is any amino acid, $X_{56}$ is any amino acid, and $X_{58}$ is any amino acid;

detecting formation of a first set of complexes comprising an antibody and one or more peptides in the first population;

contacting said sample with a second population of isolated peptides comprising at least three different peptides, each comprising a sequence of F-S-A-K-E-E-$X_7$-A-E-T-R-$X_{12}$-T-F-G-L-$X_{17}$-K-Q-Y-D-G-A-$X_{24}$-I-$X_{26}$-E-N-Q-V-Q-N-K-F-T-I-S-N-C (SEQ ID NO: 2) or a fragment thereof, wherein $X_7$ is any amino acid, $X_{12}$ is any amino acid, $X_{17}$ is any amino acid, $X_{24}$ is any amino acid, and $X_{26}$ is any amino acid; and detecting formation of a second set of complexes comprising an antibody and one or more peptides in the second population, wherein formation of both the first and second sets of complexes indicates that the subject is infected with *Ehrlichia ewingii* (*E. ewingii*), and wherein formation of the first but not the second set of complexes indicates that the subject is infected with *Ehrlichia canis* (*E. canis*) and/or *Ehrlichia chaffeensis* (*E. chaffeensis*).

2. A method for identifying the species of *Ehrlichia* infecting a subject, if present, the method comprising:

contacting a sample from the subject with a first population of isolated peptides as defined in claim 1;

detecting formation of a first set of complexes comprising an antibody and one or more peptides in the first population;

contacting said sample with a third population of isolated peptides comprising at least three different peptides, each comprising a sequence of S-$X_2$-K-E-$X_5$-K-Q-$X_8$-T-$X_{10}$-$X_{11}$-$X_{12}$-$X_{13}$-G-L-K-Q-$X_{18}$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid; and detecting formation of a third set of complexes comprising an antibody and one or more peptides in the third population, wherein formation of both the first and third sets of antibody-peptide complexes indicates that the subject is infected with *E. canis* and/or *E. chaffeensis*, and wherein formation of the first but not the third set of antibody-peptide complexes indicates that the subject is infected with *E. ewingii.*

3. The method of claim 1, wherein:

$X_{39}$ in SEQ ID NO: 1 is K;
$X_{44}$ in SEQ ID NO: 1 is K or R;
$X_{49}$ in SEQ ID NO: 1 is E or D;
$X_{56}$ in SEQ ID NO: 1 is K or Q;
$X_{58}$ in SEQ ID NO: 1 is E or T;
$X_7$ in SEQ ID NO: 2 is K;
$X_{12}$ in SEQ ID NO: 2 is K or R;
$X_{17}$ in SEQ ID NO: 2 is E or D;
$X_{24}$ in SEQ ID NO: 2 is K or Q; and/or
$X_{26}$ in SEQ ID NO: 2 is E or T.

4. The method of claim 1, wherein:

said fragment of SEQ ID NO: 1 comprises at least 20, 25, 30, 35, or 40 contiguous amino acids from SEQ ID NO: 1 and/or amino acids 33 to 71 of SEQ ID NO: 1; and/or said fragment of SEQ ID NO: 2 comprises at least 15, 20, 25, 30, or 35 contiguous amino acids from SEQ ID NO: 2.

5. The method of claim 1, wherein:

each peptide in the first population comprises a sequence of SEQ ID NO: 1; and/or each peptide in the second population comprises a sequence of SEQ ID NO: 2.

6. The method of claim 1, wherein at least one of said detecting steps comprises: (i) performing an ELISA assay; (ii) running a lateral flow assay; (iii) performing an agglutination assay; (iv) performing a Western blot, slot blot, or dot blot assay; (v) performing a wavelength shift assay; (vi) running the sample through an analytical or centrifugal rotor; or (vii) running a microarray assay.

7. The method of claim 1, wherein said sample is from a human, canine, or feline subject.

8. The method of claim 1, wherein said sample is a blood, serum, plasma, cerebral spinal fluid, tissue extract, urine, or saliva sample.

9. The method of claim 1, further comprising reporting detection results.

10. The method of claim 2, wherein:

$X_{39}$ in SEQ ID NO: 1 is K;
$X_{44}$ in SEQ ID NO: 1 is K or R;
$X_{49}$ in SEQ ID NO: 1 is E or D;
$X_{56}$ in SEQ ID NO: 1 is K or Q;
$X_{58}$ in SEQ ID NO: 1 is E or T;
$X_{39}$ in SEQ ID NO: 3 is K;
$X_{44}$ in SEQ ID NO: 3 is K or R;
$X_{49}$ in SEQ ID NO: 3 is E or D;
$X_{56}$ in SEQ ID NO: 3 is K or Q; and/or
$X_{58}$ in SEQ ID NO: 3 is E or T.

11. The method of claim 2, wherein:

said fragment of SEQ ID NO: 1 comprises at least 20, 25, 30, 35, or 40 contiguous amino acids from SEQ ID NO: 1 and/or amino acids 33 to 71 of SEQ ID NO: 1; and/or said fragment of SEQ ID NO: 3 comprises at least 20, 25, 30, 35, or 40 contiguous amino acids from SEQ ID NO: 3 and/or amino acids 33 to 71 of SEQ ID NO: 3.

12. The method of claim 2, wherein:

each peptide in the first population comprises a sequence of SEQ ID NO: 1; and/or each peptide in the third population comprises a sequence of SEQ ID NO: 3.

13. The method of claim 2, wherein at least one of said detecting steps comprises: (i) performing an ELISA assay; (ii) running a lateral flow assay; (iii) performing an agglutination assay; (iv) performing a Western blot, slot blot, or dot blot assay; (v) performing a wavelength shift assay; (vi)

running the sample through an analytical or centrifugal rotor; or (vii) running a microarray assay.

14. The method of claim 2, wherein said sample is from a human, canine, or feline subject.

15. The method of claim 2, wherein said sample is a blood, serum, plasma, cerebral spinal fluid, tissue extract, urine, or saliva sample.

16. The method of claim 2, further comprising reporting detection results.

17. The method of claim 2, wherein the sample is further analyzed with at least one assay to determine whether the infecting species is *E. canis* or *E. chaffeensis.*

18. The method of claim 17, wherein said at least one assay is an indirect immunofluorescence assay (IFA), a dot blot assay, a lateral flow assay, ELISA, or a Western Blot.

19. The method of claim 1 further comprising:

contacting said sample with a third population of isolated peptides comprising at least three different peptides, each comprising a sequence of S-$X_2$-K-E-$X_5$-K-Q-$X_8$-T-$X_{10}$-$X_{11}$-$X_{12}$-$X_{13}$-G-L-K-Q-$X_8$-W-$X_{20}$-G-$X_{22}$-$X_{23}$-$X_{24}$-$X_{25}$-$X_{26}$-G-G-G-G-G-N-F-S-A-K-E-E-$X_{39}$-A-$X_{41}$i-T-R-$X_{44}$-T-F-G-$X_{48}$-$X_{49}$-K-Q-Y-D-G-A-$X_{56}$-I-$X_{58}$-E-N-Q-V-Q-N-K-F-T-I-S-N-C (SEQ ID NO: 3) or a fragment thereof, wherein $X_2$ is an amino acid selected from the group consisting of A and V, $X_5$ is an amino acid selected from the group consisting of E and D, $X_8$ is an amino acid selected from the group consisting of T and P, $X_{10}$ is an amino acid selected from the group consisting of T and V, $X_{11}$ is an amino acid selected from the group consisting of G and A, $X_{12}$ is an amino acid selected from the group consisting of L and V, $X_{13}$ is an amino acid selected from the group consisting of Y and F, $X_{18}$ is an amino acid selected from the group consisting of D and N, $X_{20}$ is an amino acid selected from the group consisting of D and N, $X_{22}$ is an amino acid selected from the group consisting of S and V, $X_{23}$ is an amino acid selected from the group consisting of A, S, and T, $X_{24}$ is an amino acid selected from the group consisting of A and I, $X_{25}$ is an amino acid selected from the group consisting of T and P, $X_{26}$ is an amino acid selected from the group consisting of S, N, and K, $X_{39}$ is any amino acid, $X_{41}$ is an amino acid selected from the group consisting of D and N, $X_{44}$ is any amino acid, $X_{48}$ is an amino acid selected from the group consisting of V and A, $X_{49}$ is any amino acid, $X_{56}$ is any amino acid, and $X_{58}$ is any amino acid; and detecting formation of a third set of complexes comprising an antibody and one or more peptides in the third population, wherein formation of both the first and second sets of complexes but not the third set indicates that the subject is infected with *E. ewingii*, and wherein formation of both the first and third sets of complexes but not the second set indicates that the subject is infected with *E. canis* and/or *E. chaffeensis.*

20. The method of claim 19, wherein:

$X_{39}$ in SEQ ID NO: 1 is K;
$X_{44}$ in SEQ ID NO: 1 is K or R;
$X_{49}$ in SEQ ID NO: 1 is E or D;
$X_{56}$ in SEQ ID NO: 1 is K or Q;
$X_{58}$ in SEQ ID NO: 1 is E or T;
$X_7$ in SEQ ID NO: 2 is K;
$X_{12}$ in SEQ ID NO: 2 is K or R;
$X_{17}$ in SEQ ID NO: 2 is E or D;
$X_{24}$ in SEQ ID NO: 2 is K or Q;
$X_{26}$ in SEQ ID NO: 2 is E or T,
$X_{39}$ in SEQ ID NO: 3 is K;
$X_{44}$ in SEQ ID NO: 3 is K or R;
$X_{49}$ in SEQ ID NO: 3 is E or D;
$X_{56}$ in SEQ ID NO: 3 is K or Q; and/or
$X_{58}$ in SEQ ID NO: 3 is E or T.

21. The method of claim 19, wherein:

said fragment of SEQ ID NO: 1 comprises at least 20, 25, 30, 35, or 40 contiguous amino acids from SEQ ID NO: 1 and/or amino acids 33 to 71 of SEQ ID NO: 1;

said fragment of SEQ ID NO: 2 comprises at least 15, 20, 25, 30, or 35 contiguous amino acids from SEQ ID NO: 2; and/or said fragment of SEQ ID NO: 3 comprises at least 20, 25, 30, 35, or 40 contiguous amino acids from SEQ ID NO: 3 and/or amino acids 33 to 71 of SEQ ID NO: 3.

22. The method of claim 19, wherein:

each peptide in the first population comprises a sequence of SEQ ID NO: 1;

each peptide in the second population comprises a sequence of SEQ ID NO: 2; and/or each peptide in the third population comprises a sequence of SEQ ID NO: 3.

23. The method of claim 19, wherein said sample is from a human, canine, or feline subject.

24. The method of claim 19, wherein said sample is a blood, serum, plasma, cerebral spinal fluid, tissue extract, urine, or saliva sample.

25. The method of claim 19, wherein at least one of said detecting steps comprises: (i) performing an ELISA assay; (ii) running a lateral flow assay; (iii) performing an agglutination assay; (iv) performing a Western blot, slot blot, or dot blot assay; (v) performing a wavelength shift assay; (vi) running the sample through an analytical or centrifugal rotor; or (vii) running a microarray assay.

26. The method of claim 19, further comprising reporting detection results.

27. The method of claim 19, wherein the sample is further analyzed with at least one assay to determine whether the infecting species is *E. canis* or *E. chaffeensis.*

28. The method of claim 1, wherein at least one of the isolated peptides in the first population of isolated peptides comprises a sequence, or a fragment thereof, selected from the group consisting of SEQ ID NOs: 4, 6, 7, 8, 10, 11, 13, 14, 16, and 17.

29. The method of claim 1, wherein at least one of the isolated peptides in the second population of isolated peptides comprises a sequence, or a fragment thereof, selected from the group consisting of SEQ ID NOs: 53, 55, 57, 61, and 64.

30. The method of claim 2, wherein at least one of the isolated peptides in the third population of isolated peptides comprises a sequence, or a fragment thereof, selected from the group consisting of SEQ ID NOs: 67, 70, 71, 73, 75, 76, 77, 78, 79, and 81.

* * * * *